US005744151A

United States Patent [19]

Capelli

[11] Patent Number: 5,744,151
[45] Date of Patent: Apr. 28, 1998

[54] SILVER-BASED PHARMACEUTICAL COMPOSITIONS

[76] Inventor: Christopher C. Capelli, 4500 7th. St., Kenosha, Wis. 53144

[21] Appl. No.: 671,897

[22] Filed: Jun. 27, 1996

Related U.S. Application Data

[60] Provisional application No. 60/000,739 Jun. 30, 1995.
[51] Int. Cl.$^6$ .................. A01N 25/02; A01N 59/16
[52] U.S. Cl. .................. 424/405; 424/78.34; 424/404; 424/409; 424/411; 424/422; 424/423; 424/430; 424/434; 424/446; 424/447; 424/618; 604/890.1
[58] Field of Search .................. 424/404, 405, 424/409, 411, 422, 423, 434–437, 445–447, 78.34, 78.07, 618, 430; 604/890.1

[56] References Cited

U.S. PATENT DOCUMENTS

| 3,092,552 | 6/1963 | Romans | 167/72 |
|---|---|---|---|
| 3,339,546 | 9/1967 | Chen | 128/156 |
| 3,761,590 | 9/1973 | Fox | 424/470 |
| 3,857,934 | 12/1974 | Berinstein et al. | 424/411 |
| 4,451,447 | 5/1984 | Kaplan et al. | 424/131 |
| 4,581,028 | 4/1986 | Fox, Jr. et al. | 623/2 |
| 5,045,601 | 9/1991 | Capelli et al. | 525/327.1 |
| 5,147,339 | 9/1992 | Sundstrom | 604/307 |
| 5,326,567 | 7/1994 | Capelli | 424/405 |
| 5,429,819 | 7/1995 | Oka et al. | 424/405 |
| 5,438,076 | 8/1995 | Friedman et al. | 514/772.6 |
| 5,503,840 | 4/1996 | Jacobson et al. | 424/421 |
| 5,532,290 | 7/1996 | Newington et al. | 523/122 |

OTHER PUBLICATIONS

CAS Abstract No. 106:182654 (JP 61289036; Dec. 19, 1986).

WPIDS Abstact No. 92–187552 (JP 04114038; Apr. 15, 1992).

Goodman and Gilman's *The Pharmacological Basis of Therapeutics* (6th edition, L.S. Goodman, A. Gilman, and A.G. Goodman, eds.) Macmillan Publishing Co. Inc., New York, p. 1100. As the Sixth edition was unavailable, Applicant is providing the corresponding pages, from the Seventh edition [Goodman and Gilman's *The Pharmacological Basis of Therapeutics*(7th edition, L.S. Goodman, A. Gilman, and A.G. Goodman, eds.) Macmillan Publishing Co. Inc., New York, pp. 1066–1071].

N. Grier, "Silver and Its Compounds" in *Disinfection, Sterilization, and Preservation*, (3rd edition S.S. Block, ed.), Lea & Febiger, Philadelphia, Ch. 20, p. 395 (1983).

J.P. Heggers and M.C. Robson, "Synergism, Antagonism, Topical Antimicrobial Combinations: An In Vitro Analysis, "JBCR 7:3 (May/Jun. 1986).

Lawrence, C. A. and Block, S. S. (eds.) *Disinfection, Sterilization and Preservation*, Lea & Febiger, Philadelphia, Chs. 24 and 28 (1968).

Tomioka et al., "Synthesis of Antimicrobial Agent Composed of Silver–Thiosulfate Complex Ion," *Nippon Kagaku Kaishi* 10:848–50 (1995).

Lowbury et al., "Topical Chemoprophylaxis with Silver Sulphadizaine and Silver Nitrate Chlorhexidine Creams: Emergence of Sulphonamide–resistant Gram–negative Bacilli," *British Medical Journal* 1:493–496 (1976).

Russell et al., Antimicicrobial Activity and Action of Silver, *Progress in Medicinal Chemistry* 31:351–70 (1994).

*Primary Examiner*—Neil S. Levy
*Attorney, Agent, or Firm*—Medlen & Carroll, LLP

[57] ABSTRACT

The present invention relates to pharmaceutical compositions which are photostable and antimicrobially active comprising one or more medicinal agents and a stabilized ionized silver-based antimicrobial composition. The stabilized ionized silver-based antimicrobial composition comprises a stabilizing acyclic polyether polymer, cations, and anions present in excess with regard to the amount of cations. Methods for making and using the pharmaceutical compositions are also described. These pharmaceutical compositions are useful in the prevention and treatment of infections and diseases.

23 Claims, No Drawings

SILVER-BASED PHARMACEUTICAL COMPOSITIONS

This application for patent under 35 U.S.C. § 111(a) claims priority to Provisional Application Ser. No. 60/000, 739, filed Jun. 30, 1995, now abandoned, under 35 U.S.C. § 111(b).

FIELD OF THE INVENTION

The present invention relates generally to pharmaceutical compositions and processes for making thereof and, in particular, to photostable and antimicrobially-active pharmaceutical compositions comprising the combination of one or more medicinal agents and a stable ionized silver-based antimicrobial composition and processes for making thereof.

BACKGROUND OF THE INVENTION

I. The Emergence of Drug Resistance

Topical antimicrobials are currently prescribed by healthcare providers to prevent and treat a variety of serious skin infections such as impetigo, infected diabetic ulcers, venous stasis ulcers, infected surgical wounds, burns, acne, psoriasis and other topical infections. One of the most ominous problems facing modern medicine is the development of bacteria that are resistant to being killed by antimicrobial agents. Increasingly, topical antimicrobials that contain antibiotics are not effective against microbes which have developed drug resistance (i.e., antibiotic-resistant microbes).

Drug resistance is usually caused by a mutation within the microbe. When a colony of microbes is subjected to a dose of an antimicrobial, most of the bacteria die. However, occasionally some microbes, by chance, harbor mutant genes that render them immune to the antimicrobial drug. Not only do these bacteria survive the antimicrobial treatment, but they transfer their "drug resistant" genes to their progeny (one bacterium can leave approximately 17,000,000 offspring within 24 hours). As a result, a specific antibiotic or antimicrobial used to treat an infection caused by that microbe may no longer be effective. Furthermore, once a microbe develops resistance to a specific antimicrobial, there is the possibility that the microbe will concomitantly be resistant to the entire class of antimicrobials.

Certain antimicrobials, especially antibiotics, are becoming increasingly ineffective due to the rapid increase in drug-resistant forms of microbes. For example, mupirocin ointment (Bactroban®, SmithKline Beecham) is a topical antimicrobial used most frequently for treatment of impetigo. Mupirocin has been shown to be highly effective against *Staphylococcus aureus*, *S. epidermidis*, *S. saprophyticus*, and *Streptococcus pyogenes*. Unfortunately, microbes frequently develop drug resistance to mupirocin. As a result, widespread use of mupirocin as a topical antimicrobial is being hampered.

II. Use of Combinations of Antimicrobial Agents to Prevent Drug Resistance

A well known method to prevent the loss of a drug's antimicrobial efficacy by emergence of drug-resistant microbes is through the use of two or more antimicrobial agents in combination. The rationale is that if spontaneous mutation is the predominant means by which microorganisms acquire resistance to antibiotics, combination therapy should be an effective means of preventing resistance. For example, if the frequency of mutation for the acquisition of resistance to one drug is $10^{-7}$ and that for a second drug $10^{-6}$, the probability of independent mutation causing resistance to both drugs in a single microbe is the product of the two frequencies, $10^{-13}$. This makes the emergence of such mutant resistant strains statistically unlikely. [See, e.g., Goodman, A. Gilman's *The Pharmacological Basis of Therapeutics*(6th edition, L. S. Goodman, A. Gilman, and A. G. Goodman, eds.) Macmillan Publishing Co. Inc., New York, p. 1100]. An example of using two or more drugs in combination to prevent the development of drug resistance during the course of therapy involves the combination of isoniazid and rifampin for the treatment of tuberculosis.

In developing antimicrobial pharmaceutical compositions consisting of two or more different antimicrobial agents, it is best to use at least one antimicrobial agent having a broad spectrum of antimicrobial activity. In this way, while making the composition less prone to the formation of drug resistance, the specific antimicrobial activity of one agent is complemented by the broad-spectrum antimicrobial activity of the other agent.

III. Topical Silver-Containing Agents

A. Characteristics Of Ionized Silver

In developing topical antimicrobial pharmaceutical compositions consisting of two different antimicrobial agents, ionized silver is one preferred agent. Silver, in its ionic state, is inherently safe and possesses a very broad spectrum of antimicrobial efficacy. Specifically, ionized silver has broad antibacterial, antifungal and antiviral properties. [N. Grier, "Silver and Its Compounds" in *Disinfection, Sterilization, and Preservation*, (3rd edition S. S. Block, ed.), Lea & Febiger, Philadelphia, Ch. 20, p. 395 (1983)]. Additionally, being oligodynamic, ionized silver can provide long-lasting, or "residual", antimicrobial protection.

The broad spectrum of antimicrobial activity of ionized silver is caused by the reactivity of silver ions with a variety of functional groups. Silver ions, similar to most heavy metals in their ionized state, can complex with electron-donating functional groups containing sulfur, oxygen or nitrogen. In biological systems these electron donor groups are present as functional groups such as thiols, carboxylates, phosphates, hydroxyl, amines, imidazoles and indoles, either singly or in many varied combinations. These electron donor groups are found in great numbers in a variety of biomolecules which make up microbes. The binding of ionized silver to any of these electron donor groups causes disruption or inactivation of the biological system, resulting in the microbe's death. Depending on the source of the silver ions, studies indicate that silver ions kill the microbe either by attacking the cell wall and membrane producing blebs or by producing aggregation of nuclear material into filaments. [N. Grier, "Silver and Its Compounds" in *Disinfection, Sterilization, and Preservation*, (3rd edition S. S. Block, ed.), Lea & Febiger, Philadelphia, Ch. 20, p. 395 (1983)].

B. Currently Used Preparations Containing Ionized Silver

The medical use of ionized silver has been limited to the use of silver nitrate because of silver nitrate's ability to completely ionize in water. Silver nitrate solutions (1%) have been used as eye drops in newborn babies for years to prevent ophthalmia neonatorum. In addition, dressings wetted with 0.5% silver nitrate solution have been used to cover second- and third-degree burns to prevent and treat infections. Unfortunately, silver nitrate solutions are very photo-unstable and will leave a dark stain on anything with which they come into contact; therefore, they are not widely utilized.

U.S. Pat. No. 3,092,552 to Romans discloses the use of silver ions as an oligodynamic agent in a therapeutic or surface-treating composition or as a means for germicidally protecting an article or surface. Specifically, the disclosed composition is comprised of a low concentration of a silver compound such as silver nitrate or silver oxide, a reducing agent such as starch or sugar, polyethylene glycol (PEG), and urea. Though the patent teaches that the addition of small amounts of sodium chloride or cupric chloride to the composition prevents discoloration, even when the product is exposed to sterilization procedures and direct sunlight, it has been demonstrated that the silver ion compositions are not photostable. [See U.S. Pat. 5,326,567 to Capelli, hereby incorporated by reference].

C. Compositions Containing Ionized Silver

Numerous attempts have been made to develop antimicrobial pharmaceutical compositions which combine one or more antimicrobial agents with either ionized silver derived from a silver nitrate solution, or a silver salt such as silver sulfadiazine. As described below, these attempts have had limited success.

U.S. Pat. No. 3,761,590 to Fox attempted to improve on the shortcomings of silver nitrate solutions by complexing the silver ion to the antibiotic sulfadiazine to form silver sulfadiazine. Silver sulfadiazine is a non-ionized, water-insoluble powder which is administered as a 1% cream to prevent bacterial infection in the treatment of burns. [N. Grier, "Silver and Its Compounds" in *Disinfection, Sterilization, and Preservation*, (3rd edition S. S. Block, ed.), Lea & Febiger, Philadelphia, Ch. 20, p. 395 (1983)]. While compositions containing silver sulfadiazine are non-staining and have greatly improved photostability over ionized silver, they are less than ideal because the silver is in the form of a silver salt and not in the form of ionized silver. As a result, silver ions must be ionized off the silver sulfadiazine salt powder in order to be antimicrobially active.

Pharmaceutical compositions which combine one or more antimicrobial agents with ionized silver derived from silver nitrate are still associated with the problems of photoinstability and staining. For example, Lowbury et al studied the use of pharmaceutical compositions consisting of chlorhexidine gluconate (0.2%) and silver nitrate (0.5%) in a cream base. The compositions rapidly turned brown or black upon exposure to light.

Though pharmaceutical compositions which combine one or more antimicrobial agent with a silver salt are more photostable and less prone to causing staining, they have problems regarding predictable antimicrobial efficacy. That is, when a silver salt is combined with another antimicrobial agent, it cannot readily be predicted whether the silver salt will be antagonistic, thereby resulting in the loss of all antimicrobial activity. For example, Heggers and Robson investigated the in vitro effects (i.e., synergism, antagonism, or no effect) of topical creams made by combining silver sulfadiazine with one of two antimicrobial agents, mafenide acetate or nitrofurazone. [J. P. Heggers and M. C. Robson, "Synergism, Antagonism, Topical Antimicrobial Combinations: An In Vitro Analysis," JBCR 7:3 (May/June 1986)]. Though synergistic effects were noted against *P. aeruginosa*, the combination of silver sulfadiazine with either mafenide acetate or nitrofurazone was largely antagonistic (i.e., the addition of the silver salt resulted in a loss of antimicrobial activity) when tested against *S. aureus* and *Escherichia coli*. The loss of antimicrobial activity is probably the result of ionic silver present in the pharmaceutical composition reacting with the medicinal agent, thereby depleting the effective concentration of silver ions.

Moreover, while the high reactivity of ionized silver provides a broad spectrum of antimicrobial efficacy, it also results in the ionized silver being incompatible and generally unstable when incorporated in a composition with a number of different medicinal agents. This is especially true if the medicinal agents have an electron donor functional group with which the ionized silver can complex. As a result, the presence of ionic silver in a composition containing a medicinal agent often causes the precipitation and inactivation of both the medicinal agent and the ionized silver.

From the above, it should be clear that the presently-available silver-based antimicrobial compositions have limited applications, often quickly lose their antimicrobial efficacy, and are frequently unstable. What is needed are pharmaceutical compositions useful in the prevention and treatment of infections and diseases which comprise an antimicrobial agent and one or more medicinal agents and which remain antimicrobially active.

SUMMARY OF THE INVENTION

The present invention relates generally to photostable, nonstaining, antimicrobially-active pharmaceutical compositions comprising one or more medicinal agents and ionized silver for use in topical applications in the prevention and treatment of diseases.

The use of antimicrobially-active pharmaceutical compositions containing silver in a fully ionized form provides the compositions with a broad spectrum of antimicrobial protection without the additional step of ionizing the silver from the silver salt in order to make it antimicrobially active. Besides being photostable and non-staining, the antimicrobially-active pharmaceutical compositions comprising ionized silver in combination with an antimicrobial medicinal agent are less vulnerable to the formation of drug-resistant microbes. Furthermore, such pharmaceutical compositions provide antimicrobial activity which is long lasting because of the residual antimicrobial activity that ionized silver provides; this long-lasting effect may decrease the number of applications of the composition necessary in order to treat or prevent infection.

The present invention also provides methods for making photostable, nonstaining, antimicrobially-active pharmaceutical compositions comprising one or more medicinal agents and ionized silver. The medicinal agents may be antimicrobial agents, topically active drugs (e.g., local anesthetics or anti-pruritics), or systemically active drugs (e.g., sedatives and hormones).

The present invention provides methods by which pharmaceutical compositions comprising one or more medicinal agents and ionized silver may be used to treat medical devices so as to provide infection-resistant medical devices for use in the treatment and prevention of infections and diseases in mammals. Such methods are especially important in that the use of medical devices can be associated with multiple problems (e.g., pain, inflammation, allergic reactions, and infection). Furthermore, the pharmaceutical compositions of the present invention are useful in making infection-resistant cosmetics and infection-resistant personal care products.

The photostable and antimicrobially-active pharmaceutical compositions of the present invention generally contain one or more medicinal (i.e., pharmaceutical) agents combined with a stabilized silver ion-based antimicrobial composition wherein the stabilized silver ion-based antimicrobial composition comprises: a) a stabilizing acyclic polyether polymer; b) silver ions or other cations; and c) a stabilizing anion, wherein the anion is present in excess with regard to the amount of silver ions or other cations. The pharmaceutical compositions may be used to treat an infection or disease in mammals, including humans, by applying to the site of infection or disease an effective amount of the pharmaceutical composition.

DEFINITIONS

To facilitate understanding of the invention set forth in the disclosure that follows, a number of terms are defined below.

As used herein, the term "topically" means application to the surface of the skin, mucosa, viscera, etc.

As used herein, the term "topically active drugs" indicates a substance or composition which elicits a pharmacologic response at the site of application but which is not necessarily an antimicrobial agent.

As used herein, the term "systemically active drugs" is used broadly to indicate a substance or composition which will produce a pharmacologic response at a site remote from the point of application.

As used herein, the term "medical devices" includes any material or device that is used on, in, or through a patient's body in the course of medical treatment for a disease or injury. Medical devices include, but are not limited to, such items as medical implants, wound care devices, drug delivery devices, and body cavity and personal protection devices. The medical implants include, but are not limited to, urinary catheters, intravascular catheters, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incise drapes. Drug delivery devices include, but are not limited to, drug delivery skin patches, drug delivery mucosal patches and medical sponges. Body cavity and personal protection devices, include, but are not limited to, tampons, sponges, surgical and examination gloves, and toothbrushes. Birth control devices include, but are not limited to, IUD's and IUD strings, diaphragms and condoms.

DESCRIPTION OF THE INVENTION

The present invention relates generally to pharmaceutical compositions and processes for making thereof and, in particular, to photostable and antimicrobially-active pharmaceutical compositions comprising the combination of one or more medicinal agents and a stabilized, ionized silver-based antimicrobial composition and processes for making thereof. These pharmaceutical compositions are intended for topical application in the prevention and treatment of infections and diseases and can also be used in conjunction with medical devices, cosmetics and personal care products to make them infection-resistant.

The description of the invention is divided into the following parts: I) Ionized Silver-Based Compositions; II) Pharmaceutical Compositions Containing Ionized Silver-Based Compositions And Medicinal Agents; III) Topical Applications For The Pharmaceutical Compositions; and IV) Use of the Pharmaceutical Compositions In Conjunction With Medical Devices.

I. IONIZED SILVER-BASED COMPOSITIONS

A. Characteristics Of Ionized Silver-Based Compositions

As set forth above, the pharmaceutical compositions of the present invention comprise the combination of i) one or more medicinal agents and ii) a stabilized, ionized silver-based composition. This section addresses the characteristics of the ionized-silver-based compositions, and the sections that follow describe the components and methods used to produce the compositions.

The preferred ionized silver-based compositions of the present invention include at least the following components:

(a) a stabilizing acyclic polyether polymer;

(b) silver ions; and (c) a stabilizing anion, wherein the anion is present in excess with regard to the amount of silver ions.

These antimicrobial ionized silver-based compositions are stabilized such that the silver ions within the compositions are photostable. Though it is not necessary that the particular method of producing photostable compositions be understood in order to practice the present invention, it is believed that this photostability is achieved through the formation of a "host-guest relationship" wherein the acyclic polyether is the "host" and the silver cation is the "guest". The stabilization of this "host-guest relationship" is accomplished through the use of excess anions in relation to the amount of silver ions.

The silver ions maintain their antimicrobial activity even though the silver ions are stabilized so that the ionized silver-based composition does not discolor when exposed to light. As previously stated, the antimicrobial activity of silver is caused by the reactivity of ionized silver with various biological functional groups. Silver ions, similar to most heavy metals in their ionized state, can complex with electron donor groups containing sulfur, oxygen or nitrogen. In biological systems, these electron donor groups are present as biological functional groups such as thiols, carboxylates, phosphates, hydroxyl, amines, imidazoles, and indoles, either singly or in varied combinations. These electron donor groups are found in great numbers in a variety of biomolecules which make up microbes. The binding of ionized silver to any of these electron donor groups causes disruption or inactivation of the biological system, resulting in death of the microbes.

B. Components Of Ionized Silver-Based Compositions

ACYCLIC POLYETHERS

As indicated above, the ionized silver-based compositions used in the production of the pharmaceutical compositions of the present invention comprise acyclic polyethers. Suitable acyclic polyethers for use in the compositions include polyethylene glycol [H(OCH$_2$CH$_2$)$_n$—OH], polypropylene glycol [H(OCH(CH$_3$)CH$_2$)$_n$—OH], and copolymers of polyethylene glycol and polypropylene glycol such as those marketed under the trademark Pluronics® by BASF (Ludwigschafen, Germany). The preferred acyclic polyether polymers are those of the polyethylene glycol (PEG) class.

Polyethylene glycols can be regarded chemically as polyether diols made by the stepwise addition of ethylene oxide to water or ethylene glycol starter to form long, linear chains of oxyethylene (O—CH$_2$CH$_2$) units having primary hydroxyl groups at each end. Depending upon chain length, the polyethylene glycols range in physical appearance at room temperature from water-white viscous liquids (M.W. 200 to 700), to waxy semi-solids (M.W.>1000 to 2000), to hard, wax-like solids (M.W. 3000 to 20,000 and above). PEGs are soluble in water, very low in toxicity, and nonirritating. Furthermore, they possess wide compatibility with other substances and good solvent action, stability, and lubricity.

The preferred polyethers are those of the glycol polyether class. These polyethers have the greatest ability to form a "host" configuration. Because they are not structurally constrained by their carbon backbone, they form a stable coil configuration about a silver cation more easily than other polyethers. Though polypropylene glycol will form a "host" configuration, it is more hindered than PEG since it has an extra methyl group projecting from its carbon chain and is therefore less preferred.

As noted above, the silver ion is thought to be stabilized through the formation of a "host-guest relationship" with the polyether. The polyether becomes the "host" through the formation of a pseudo-crown ether. That is, the polyether forms a coil, the center of which has ether groups internalized and carbon groups externalized in a conformation similar to cyclic crown ethers. The size of the pseudo-crown formed by the coiling polyether will influence the ability of the polyether to form a "host-guest relationship" with the silver ion. If the crown is too large, the silver ion will not be effectively stabilized; if the crown is too small, the silver ion will not be able to act as a "guest" ion.

The chain length of the polyether also plays an important role in stabilizing the cation. If the polyether is relatively small, it will not be able to form a complete coil or will form a coil which is too small for the formation of a "host-guest relationship" with the silver cation. Based on the size of the silver cation (approximately 2.52 Å), it is believed that a polyether with at least six monomers is required. Six ether groups would result in a polyether polymer with a molecular weight of 282 Daltons. Polyether glycols are available usually as a mixture of several molecular weights having a Gaussian distribution centered at a specific molecular weight. For example, PEG 300 has an average molecular weight of 300 Daltons (i.e., a Gaussian distribution centered at 300 Daltons including PEGs with molecular weights both below and above 300 Daltons).

In order to stabilize the silver cation, the preferred PEGs should have a molecular weight of 300 Daltons or greater. Because PEG 300 will have a portion of its composition made up of smaller PEGs, it would not be expected to stabilize as many silver cations because only those PEGs with a molecular weight greater than 282 Daltons will contribute to the formation of the "host-guest relationship". By way of further comparison, PEG 200 contains polymers with an average molecular weight less than 282 Daltons, and therefore would not be expected to stabilize more than a small number of silver cations.

Thus, the preferred polyether is polyethylene glycol having a molecular weight in the range of 200 to 100,000 Daltons, and even more preferably in the range of from 300 to 10,000 Daltons.

IONIZED SILVER

The silver ion used in the stabilized ionized silver-based compositions can be derived from silver salts such as silver nitrate, silver chloride, silver acetate, silver bromide, etc. The preferred silver salt for use in making the ionized silver-based compositions is silver nitrate.

U.S. Pat. No. 5,326,567 to Capelli (previously incorporated by reference) also teaches the use of many other metal cations. These metal cations include all metal compounds that are physiological, antimicrobial compounds, and, in particular, metal compounds which are "oligodynamic." The term "oligodynamic" is used to denote a metal agent, particularly a metal salt or a metal ion it yields upon dissociation, that has antimicrobial activity in very small quantities. The "oligodynamic" metals include the precious metals, such as silver, gold and platinum; and other metals such as copper, zinc, cerium, and gallium. As previously stated, the preferred oligodynamic metal ion is the silver ion. [See *Disinfection, Sterilization and Preservation*, Lea & Febiger, Philadelphia, Chs. 24 and 28 (1968) for a review of oligodynamic metals].

The amount of ionized silver used in the stabilized ionized silver-based composition is determined by the amount of polyether present, the size of the polyether, and the amount of anions present. The formation of a "host-guest relationship" between the polyether polymer and the silver cation forms the basis of the complexation of the silver cation. The optimal stability of the complex is obtained when there are at least five to eight ether groups per metal cation. Thus, a non-hindered polyether molecule with six ether groups should theoretically bind one silver cation ion at its upper limit, i.e., one mole of polyether molecules that have six ether groups per molecule should be able to stabilize one mole of silver cations. Any amount of silver cations below this ratio is acceptable. However, silver cations in excess of this amount will precipitate with the anions in the ionized silver-based compositions and are therefore not stable.

When the polyether polymer composition is composed of molecules which have substantially larger molecular weights (either alone or as part of a larger molecule such as a polyether urethane), and therefore have greater than six ether groups per molecule, the amount of cations that can be stabilized is more closely related to the number of polyether molecules than to the number of ether groups per molecule. For example, a polyether that has twenty ether groups per molecule will more likely bind a single metal cation, rather than three metal cations as would be predicted by the previous discussion. Though an understanding of the mechanism underlying this phenomenon is not necessary to practice the present invention, it is probably a result of the conformational limitations of the polyether molecule about the metal cation.

The preferred concentration of metal cations in the polyether compositions is in the range of from $1 \times 10^{-6}$ to $1$ mEq/gram of silver cations to polyether polymer and more preferably from $1 \times 10^{-3}$ to $1 \times 10^{-1}$ meq/gram of silver cations to polyether.

ANIONS

To form a "host-guest relationship" between the antimicrobial silver cation and the polyether molecule, an excess of anions is preferred. Suitable anions for promoting a "host-guest relationship" include the halide anions chloride, bromide, and iodide. However, the present invention is not limited to the use of halide anions. For example, thiocyanate may also be used as the anion. The most preferred anion for physiological applications is chloride because the chloride ion is the most abundant anion in the human body and has the lowest toxicity.

As previously indicated, the anions are present in excess compared to silver ions. Any source of anions may be used to provide an excess amount of the anions. Suitable sources of anions include the inorganic salts which are physiologically tolerable. These include, but are not limited to, sodium chloride, potassium chloride, sodium bromide, potassium bromide, calcium chloride, potassium iodide and sodium thiocyanate. The preferred sources of anions are sodium chloride, hydrochloric acid, or a mixture thereof.

The amount of anions to be added to the ionized silver-based composition will depend on the amount of silver cations in the final composition and which anion is being used. Due to charge density, hydrophobicity and other factors, certain anions are better at stabilizing the silver/polyether complex than others. For example, iodide is better than bromide, which is better than chloride, for stabilizing the silver polyether complex. Consequently, the amount of excess iodide required is less than the amount of excess chloride. Regardless of which anion is being used, the ratio of equivalents of anions to equivalents of metal cations should be greater than 1 to 1.

The preferred ratio of equivalents of anions to equivalents of metal cations is between 2 to 1 and 40 to 1. Minimum ratios, preferred ratios, and most preferred ratios of equivalents of various anions to equivalents of silver cations are presented in Table 1.

TABLE 1

| Anion | Minimum Ratio Of Anion to Ag$^+$ (in Eqs) | Preferred Ratio Of Anion to Ag$^+$ (in Eqs) | Most Preferred Ratio Of Anion to Ag$^+$ (in Eqs) |
|---|---|---|---|
| Chloride | >4 to 1 | 10 to 1 | 15 to 1 |
| Bromide | >2.1 to 1 | 3 to 1 | 3.5 to 1 |
| Iodide | >1.1 to 1 | 1.2 to 1 | 1.4 to 1 |

It should be noted that the amount of anions ultimately used in the compositions is dependent on the concentration of anions and the polyether used. Polyethylene glycols have a tendency to "cloud" (i.e., the PEG will precipitate out of solution) when a high concentration of salt is used. If the PEG precipitates out of solution, it is more difficult to form a stabilized silver compound.

SOLVENT

The ionized silver-based compositions of the present invention may contain a certain amount of solvent. The solvent is used to promote the solvation of the salts that provide the antimicrobial metals cations and the salts used to supply the excess amount of anions. Those salts are usually added to the solvent as solutions. Any solvent may be used which is physiologically compatible and also compatible with the metal cations, polyether polymers and the salts that provide the anions. The preferred solvents are alcohol, acetone, water and a mixture thereof; the most preferred solvent is water.

To promote the formation of the "host-guest relationship" between the polyether molecule and the silver cations, the amount of solvent used is dependent on the anion used and the amount of anion. If the concentration of the anion within the solvent, e.g., water, falls below a certain concentration, the formation of the stabilized silver composition is less likely to occur. If the anion, such as iodide, strongly promotes the formation of a silver complex, then the concentration of iodide in the water can be relatively low. If the anion, such as chloride, weakly promotes the formation of a silver complex, then the concentration of chloride in the water should be relatively high.

The amount of water to be added can be relatively high so long as the concentrations of salts are maintained. The preferred concentration of water in the final composition is between 1% and 60% and most preferably 2% and 20%. The preferred concentration of various anions within the solvents are presented in Table 2:

pharmaceutical compositions of the present invention, it is easiest to empirically determine the final stabilized ionized silver-based composition using the guidelines presented herein. Though the present invention is not limited to any particular method of making ionized silver-based compositions, an illustrative approach for making a stabilized ionized silver-based composition according to the present invention follows:

1. Preparing The Polyether

The first step is the synthesis of the particular polyether composition. An example would be the synthesis, which is well known in the art, of a low molecular weight polyether urethane. This synthesis step may be avoided if the polyether molecule is readily available and is in need of no further modification. For example one could use an ethylene glycol polymer with a molecular weight of 400 which is commercially available from a number of sources (e.g., Aldrich).

2. Making The Anion Solution

An anion from the group consisting of chloride, bromide or iodide should be chosen. If the stabilized silver composition is to be used on humans, the preferred anion is chloride. After choosing the anion, a water solution (i.e., an aqueous solution) of the anion salt should be made. The concentration of the final anion solution should be greater than the minimum concentration (see Table 2) to promote the formation of the "host-guest" relationship.

3. Making The Silver Cation Solution

A 1–5 mEq/ml silver nitrate solution in water should be made.

4. Determining The Amount And Concentration Of Anions That Can Be Used

Polyethers in the presence of appreciable amounts of dissolved salts will often show "cloud points" or temperatures above which they tend to precipitate out of solution. Since it is more difficult to form a stabilized silver composition above the "cloud point", it is important to determine the maximum concentration of dissolved anions that can be used in the final composition. This can be done empirically by preparing a series of compositions having increasing concentration of anions. For the final composition, a concentration of dissolved anions below this level should be used.

TABLE 2

| Anion | Minimum Anion/Water Concentration (meq/ml) | Preferred Anion/Water Concentration (meq/ml) | Most Preferred Anion/Water Concentration (meq/ml) |
|---|---|---|---|
| Chloride | >1.2 | >1.6 | >2.0 |
| Bromide | >0.2 | >0.4 | >0.6 |
| Iodide | >0.002 | >0.0025 | >0.004 |

C. Method Of Making Stabilized Ionized Silver-Based Compositions

Because of the number of variables involved in making a stabilized ionized silver-based composition for use in the 5. Making The Final Stabilized Ionized Silver-Based Composition a. Stir the polyether in a beaker, heating if necessary. If the polymer is a solid at room temperature, it is heated until it melts.

b. Add the anion salt solution. Use the amount determined in Step 4, supra. Mix completely.

c. Add the silver nitrate solution in small increments. Upon adding the silver nitrate solution, a precipitate will form. This precipitate will slowly dissolve with stirring. After the precipitate has dissolved, add another increment of silver nitrate solution. If the precipitate does not dissolve within 2 hours, then the maximum silver that can be used in composition has been determined. Since this maximum amount is dependent on the anion, the ratio of anion to cation, and the polyether being used, it is best determined by this empirical method.

d. Repeat steps (a) and (b), but add the amount of silver nitrate solution below the maximum determined in step (d). Mix the resulting solution. If heated, the polyether solution is then cooled to room temperature.

The silver compositions made by the procedure presented above are photostable and stain-resistant. They may be stored in a clear container in sunlight without discoloration and are stable to ultraviolet light and to a sterilizing beam of gamma radiation.

II. PHARMACEUTICAL COMPOSITIONS CONTAINING IONIZED SILVER-BASED COMPOSITIONS AND MEDICINAL AGENTS

A. Stability of the Pharmaceutical Compositions

Given the reactivity of ionized silver to biological functional groups (described above), it was expected that medicinal agents, which typically contain biological functional groups, would be incompatible in combination with a stabilized ionized silver-based composition. It has been largely assumed in the prior art that the ionized silver of the stabilized ionized silver-based composition would react (i.e., chelate and precipitate) with the added medicinal agent. Thus, it was expected that this silver-ion/medicinal agent interaction would lead to precipitation or inactivation of the medicinal agent. Furthermore, it was believed that the interaction of the medicinal agent with the ionized silver would lead to loss of photostability and antimicrobial activity of the ionized silver-based compositions. [See, e.g., J. P. Heggers and M. C. Robson, "Synergism, Antagonism, Topical Antimicrobial Combinations: An In Vitro Analysis," JBCR 7:3 (May/June 1986), as discussed above, where antimicrobial combinations of silver sulfadiazine with other topical antimicrobials were antagonistic].

Surprisingly, it was discovered that adding medicinal agents to the stabilized ionized silver-based compositions of the present invention does not visibly affect the composition. That is, the ionized silver in the stabilized ionized silver-based composition does not complex or precipitate with added medicinal agents. Furthermore, the ionized silver-based compositions surprisingly remains photostable and antimicrobially active after adding a medicinal agent.

Though the practice of the present invention does not require that the precise mechanisms of photostability, non-reactivity, and retention of antimicrobial activity described in the preceding paragraph be known, it is believed that those mechanisms may be due to the relatively small size of the medicinal agent in comparison to the size of a microbe. More specifically, the relative size of the medicinal agent in comparison to the silver/acyclic polyether complex is minor when contrasted to the relative size of a microbe in comparison to the silver/acyclic polyether complex. It is thought that the large size of a microbe affects the "host-guest relationship" of the silver/acyclic polyether complex resulting in the release of the silver ion. This free silver ion is then able to react with the functional groups on the biomolecules located within the plasma membrane of the microbe, leading to the microbe's death. By comparison, medicinal agents, with their relatively small size, do not affect the "host-guest relationship" of the silver/acyclic polyether complex. As a result, the silver ion remains stabilized within the silver/acyclic polyether complex and is unable to antagonistically react with the medicinal agent.

B. Medicinal Agents For Use In The Pharmaceutical Compositions

ANTIMICROBIAL AGENTS

The present invention contemplates the use of many diverse medicinal agents, including antimicrobial agents, topically active drugs, and systemically active drugs. The preferred medicinal agents contemplated for use in the pharmaceutical compositions of the present invention are those that can be used as antimicrobial agents in the treatment and prevention of infection and disease. Suitable antimicrobial agents include, but are not limited to, penicillin, tetracycline, oxytetracycline, chlortetracycline, chloramphenicol, chlorhexidine, mupirocin, metronidazole, miconazole, acyclovir, itraconazole and sulfonamides. Additional antimicrobial agents include antimicrobial peptides such as magainins, cecropins, protegrins, bacteriocins and defensins.

The pharmaceutical compositions of the present invention possess an additional broad spectrum of antimicrobial protection by combining antimicrobial medicinal agents in a stable fashion with ionized silver. Furthermore, as previously indicated, the use of ionized silver with the antimicrobial medicinal agent may aid in preventing the formation of drug-resistant microbes. Moreover, since silver ions are oligodynamic and are not immediately exhausted (i.e., they have a long-lasting or "residual" effect), the presence of silver ions in the pharmaceutical compositions results in compositions which are longer lasting than those containing a single antimicrobial agent.

TOPICALLY ACTIVE DRUGS

As noted above, medicinal agents besides antimicrobial agents are also contemplated for use in the pharmaceutical compositions of the present invention. These additional medicinal agents include topically active drugs for the treatment of diseases. Suitable topically active drugs include, but are not limited to, acne preparations such as isotretinoin, benzoyl peroxide, salicylic acid and tetracycline; anesthetics for topical administration such as dibucaine, lidocaine, benzocaine, tetracacine, deperodon and pramoxine hydrochloride; anti-inflammatory agents such as betamethasone benzoate, betamethasone valerate, desonide, fluocinolone acetonide, halcinonide, hydrocortisone; antiperspirants and medications used in the treatment of hyperhidrosis such as glutaraldehyde, methenamine, glycopyrrolate, scopolamine hydrobromide; antipruritic and external analgesic agents such as camphor, menthol, salicylic acid, methylsalicylate; cleansing agents such as soaps and shampoos; keratolytic, cytotoxic, and destructive agents such as anthralin, cantharidin, fluorouracil, podophyllotoxin, resorcinol; and pigmenting and depigmenting agents, sunscreens such as hydroquinone, monobenzone, trioxsalen and p-aminobenzoic acid; anabolic steroids for building up tissues under wound healing such as methandienone; proteolytic agents for the decomposition of fibrin such as trypsin; vasodilating substances for improving the flow of blow during wound healing such as tolazoline; thrombosis-hampering substances such as heparin; certain biologically active substances which affect tissue formation and tissue stabilization such as ascorbic acid and EGF (epidermal growth factor), EGF-URo (EGF-urogastron), somatostatin, somatotropin asellacrine, and TGF; and mucolytic and antiviral medicaments which are globulins such as lysozyme.

A pharmaceutical composition with a broad spectrum of antimicrobial protection is produced by combining one or more topically active drugs in a stable fashion with an ionized silver-based composition. In situations where the topically active drugs are used to treat a disease which has an abundance of dead tissue (e.g., a fungating tumor or a decubitus ulcer), the addition of antimicrobial silver ions will aid in the prevention of a secondary infection at the diseased site. Furthermore, the presence of ionized silver in the pharmaceutical composition can aid in the prevention of malodor caused by anaerobic and aerobic microbes at the diseased site. Finally, combining a topically active drug with the stabilized ionized silver-based composition minimizes the need to apply additional topical antimicrobial compositions which may be incompatible with the medicinal agent, resulting in both time and cost savings.

SYSTEMICALLY ACTIVE DRUGS

In addition to medicinal agents which are antimicrobial agents or topically active agents, the present invention also contemplates the use of systemically active drugs in the pharmaceutical compositions. The systemically active drugs are absorbed by the body surface when applied topically, either neat or with the aid of a solvent. Suitable systemically active drugs include, but are not limited to, sedatives and hypnotics such as pentobarbital sodium, phenobarbital, secobarbital sodium, carbromal, and sodium phenobarbital; psychic energizers such as 3-(2-1-aminopropyl)-indole acetate and 3-(2-aminobutyl)-indole acetate; tranquilizers such as reserpine, chlorpromazine hydrochloride, and thiopropazate hydrochloride; hormones such as adrenocorticosteroids, for example, 6-α-methylprednisolone, cortisone, cortisol, and triamcinolone; androgenic steroids, for example, methyl-testosterone, and fluoxymesterone; estrogenic steroids, for example, estrone, 17β-estradiol and ethinyl estradiol; progestational steroids, for example 17-α-hydroxyprogesterone acetate, medroxyprogesterone acetate, 19-norprogesterone, and norethindrone; and thyroxine; antipyretics such as aspirin, salicylamide, and sodium salicylate; antispasmodics such as atropine, methscopolamine bromide, and methscopolamine bromide with phenobarbital; antimalarials such as the 4-aminoquinolines, 8-aminoguinolines, and pyrimethamine; and nutritional agents such as vitamins, essential amino acids, and essential fats.

A pharmaceutical composition with a broad spectrum of antimicrobial protection is produced by combining one or more systemically active drugs in a stable fashion with an ionized silver-based composition. The addition of a stabilized ionized silver-based composition with one or more systemically active drugs to produce a pharmaceutical composition assists in the preservation of the pharmaceutical composition by protecting it from microbial proliferation and overgrowth, which could otherwise lead to spoilage of the medicinal composition containing the systemically active drugs.

C. Methods For Making Pharmaceutical Compositions

The pharmaceutical compositions of the present invention can be made using several methods. First, the pharmaceutical compositions can be made by preparing a stabilized ionized silver-based composition and then combining one or more medicinal agents with that composition. Second, the pharmaceutical compositions can be made by preparing i) an ionized silver-based composition and ii) a medicinal agent composition wherein the medicinal agent is first dissolved in an acyclic polyether polymer composition, and then combining the stabilized ionized silver-based composition and the medicinal agent composition. Third, the pharmaceutical compositions can be made by preparing i) an ionized silver-based composition and ii) a medicinal agent composition wherein the medicinal agent is first dissolved in a suitable solvent such as water or alcohol, and then adding the medicinal agent composition into the stabilized ionized silver-based composition. Each of these methods is described in more detail below.

The amount of medicinal agent or agents used in the pharmaceutical composition should be sufficient to provide a therapeutically-effective dose of the medicinal agent or agents. Similarly, the concentration of the ionized silver in the stabilized ionized silver-based composition is effective to provide antimicrobial activity to the pharmaceutical composition. The preparation of the stabilized ionized silver-based composition is described in U.S. Pat. No. 5,326,567 to Capelli (previously incorporated by reference).

The first method for preparing the pharmaceutical compositions involves preparing a stabilized ionized silver-based composition and then combining one or more medicinal agents with that composition. The medicinal agents (described above) are added directly into the stabilized ionized silver-based composition. The resulting pharmaceutical composition is then stirred until the medicinal agent is either homogeneously mixed or dissolved in the stabilized ionized silver-based composition.

In the second method set forth above, the medicinal agents to be used in the pharmaceutical compositions of the present invention are dissolved or mixed into an acyclic polyether composition which is then combined with the stabilized ionized silver-based composition. The pharmaceutical composition is then stirred until the medicinal agent composition and the stabilized ionized silver-based composition are homogeneously mixed.

In the final method set forth above, the medicinal agent to be used in the pharmaceutical compositions of the present invention is dissolved in a suitable solvent such as water or alcohol. The resulting dissolution solution is then added into the stabilized ionized silver-based composition. The pharmaceutical composition is then stirred until the medicinal agent is either homogeneously mixed or dissolved.

If the pharmaceutical compositions produced by the methods described above are to be in the form of a cream or ointment, heat may be used to aid in the mixing and stirring.

III. TOPICAL APPLICATIONS FOR THE PHARMACEUTICAL COMPOSITIONS

When in the form of a solution, cream or ointment, the pharmaceutical compositions of the present invention can be used topically on skin, in wounds, in the eyes, nose or the mouth etc. for the treatment or prevention of a large number of topical infections. For the treatment or prevention of infections in wounds, the pharmaceutical compositions can be applied to the wound site by standard methods known to the industry; one method is to apply the pharmaceutical compositions by gloved hand. Wound dressings may be used in conjunction with the pharmaceutical compositions as currently practiced in the treatment of topical infections.

In addition to the therapeutic activity of the medicinal agent used, these pharmaceutical compositions provide long-term antimicrobial protection. In the treatment of eye infections, the pharmaceutical compositions, in the form of a solution or a cream, can be applied to the lower eyelid of the patient using standard techniques. Alternatively, the pharmaceutical compositions may be in the form of an eyewash and applied using standard techniques. In the treatment of mouth infections, including gingivitis, the pharmaceutical compositions in the form of a solution or cream can be applied using a sponge applicator or a toothbrush. The pharmaceutical compositions of the present invention may also be in the form of a solution and used for infusion into a body cavity to treat infection. Furthermore, these pharmaceutical compositions can be used in cosmetics and other personal care products to make them infection-resistant.

IV. USE OF THE PHARMACEUTICAL COMPOSITIONS IN CONJUNCTION WITH MEDICAL DEVICES

A. Problems Associated With The Use Of Medical Devices And Means For Alleviating The Problems As previously indicated, the term "medical devices" includes, but is not limited to, such items as medical implants, wound care devices, drug delivery devices, and body cavity and personal protection devices. A patient can experience a number of problems when using a medical device, including local inflammation, allergic reactions, pain, and infections. For example, with the use of sutures, catheters, drainage tubes, etc., local inflammation is typically found at the site of the tissue/medical device interface. This local inflammation is usually due to the normal reaction of the tissue to the presence of a foreign body. Local inflammation can lead to tissue death at the tissue/medical device interface, failure of the medical device, and discomfort to the patient.

Similarly, allergic reactions can result from the use of medical devices like wound dressings or medical tapes. The allergic reactions are usually the result of patient sensitivity to the adhesives used in those devices. The symptoms caused by an allergic reaction can range from a mild local dermatitis to a catastrophic shock reaction leading to patient death. If a patient is found to be sensitive to the medical device, the use of the specific medical device should be discontinued; unfortunately, in a case where that specific medical device is critical to the patient's well-being, discontinuing its use may not be an option.

When a medical device is used at a site of trauma, e.g., the use of a dressing for a burn wound, pain can result. Pain can also result when the medical device is used for a long duration. For example, the use of an intravascular catheter at a peripheral site (i.e., arm. leg, ankle, etc.) for more than 2 to 5 days may result in localized pain. Severe pain caused by a medical device can lead to the premature removal or discontinuation of use of that medical device. This not only increases health care costs, but is also inconvenient to the patient and health care provider.

Finally, the major problem associated with the use of medical devices is infection due to microbes which colonize the surfaces of the materials that make up a medical device. After a medical device has become colonized, eradication of the microbes by the patient's immune response is difficult, if not impossible. Furthermore, once colonized, the contaminated medical devices can act as reservoirs for microbes. These microbial reservoirs can then "seed" into the patient's body or wound, leading to infection.

One approach to minimizing many of the problems associated with medical devices is to make them more "bioactive". In this approach, medical devices are made more responsive, or "active", to the surrounding tissue environment at the tissue/medical device interface. Making medical devices more bioactive is usually accomplished through the incorporation of a medicinal agent into the medical device. When released from the medical device, the medicinal agent can provide some therapeutic relief for a particular problem (e.g., inflammation, pain, etc.) caused by the medical device. For example, incorporating hydrocortisone into the medical device may minimize the problem of local inflammnation. Similarly, incorporating an antihistamine or a steroid like hydrocortisone may prevent an allergic reaction resulting from the adhesive of a wound dressing. Additionally, topical anesthetics can be incorporated into foam dressings to minimize pain at a burn site.

Moreover, the surface or the material of the medical devices can be made infection-resistant, thereby substantially increasing the patient's safety while using the medical device. One approach to making medical devices infection-resistant is through the incorporation of antimicrobial agents into the medical devices.

B. Incorporating The Pharmaceutical Compositions Into Medical Devices

Due to their light stability, nonstaining, and antimicrobial properties, the pharmaceutical compositions of the present invention would be useful in making infection-resistant medical devices. Surprisingly, it was found that pharmaceutical compositions containing one or more medicinal agents and ionized silver can be used to treat medical devices and can be incorporated into medical devices to render them infection-resistant. The medical devices incorporating the pharmaceutical compositions are useful in the treatment and prevention of infections and diseases in mammals.

Producing medical devices which contain one or more medicinal agents and a stabilized ionized silver-based composition using the pharmaceutical compositions of the present invention depends largely upon the construction of the medical device. If the medical device is constructed so that an adhesive material (e.g., medical tape, thin film dressing, etc.) interfaces with the tissue site, the pharmaceutical compositions can be incorporated directly into the adhesive material. Conversely, if the medical device is constructed so that a non-adherent material (e.g., medical implants such as catheters and shunts, non-adherent dressings such as alginate dressings and cellulosic dressings, etc.) interfaces with the tissue site, the pharmaceutical compositions can be applied to or incorporated into the surface of the medical device. Finally, if the medical device is made so that it has an absorbent polymer matrix (e.g., foam dressings, hydrocolloid dressings, etc.) which interfaces with the tissue site, the pharmaceutical compositions can be incorporated into the absorbent polymer matrix of the medical device.

Techniques for incorporating or applying the pharmaceutical compositions of the present invention to medical devices are well known in the art. Though the present invention is not limited to any particular methods of incorporation, a discussion of some of the techniques of incorporating or applying the pharmaceutical compositions to medical devices follows.

ADHESIVES

The pharmaceutical compositions of the present invention, especially those in the form of high viscosity liquids, can be used to produce adhesive materials which contain both a medicinal agent and a stabilized ionized silver-based composition that is both antimicrobially active and photostable. These adhesive materials can be used, e.g., as backings for wound dressings and medical tapes.

The adhesive materials used can be formulated from various polymers including, but not limited to, pressure-sensitive adhesives made from acrylic acid-derived resins such as polyacrylics, poly(alkyl)acrylates, poly(alkoxy) acryclates, polyacrylamides, poly(alkyl)acrylamides, poly(alkoxy)acrylamides, and the like. An illustrative list of such polymers includes polymeric acrylic acid esters with alcohols such as n-butanol, n-pentanol, isopentanol, 2-methyl butanol, 1-methyl butanol, 1-pentanol, 3-methyl pentanol, 2-ethyl butanol, isooctanol, and n-dodecanol, as either homopolymers or copolymerized with ethylenically-unsaturated monomers such as acrylic acid, methacrylic acid, acrylamide, methacrylamide, n-alkoxymethyl acrylamides, n-alkoxymethyl methacrylamides, tert-butylacrylamide, itaconic acid, vinylacetate, n-branched alkyl maleamic acids wherein the alkyl group has 10 to 24 carbon atoms, glycol diacrylates or mixtures thereof, polyacrylates, polyolefins, silicone adhesives, polyvinyl ethers, polyesters, polyacrylics, polyurethanes, and the like, as well as copolymers thereof.

The actual choice of the adhesive is largely dependent on the end use. It will be appreciated by those skilled in the art that the adhesive components described above might also include various chemical modifiers so as to enable the adhesive components to be usable in a variety of situations. Such chemical modifiers include, but are not limited to, tackifiers, cross-linkers, stabilizers, initiators, and the like.

The preferred adhesive of the present invention is that which is described in U.S. Pat. No. 5,045,601 to Capelli, which is hereby incorporated by reference for its teaching of the adhesive. The adhesive composition described in U.S. Pat. No. 5,045,601 comprises a polyurethane polymer adhesive, soluble or dispersible in water, that is low-temperature curable to form a solid which is a single phase at ambient temperature. The adhesive is pressure-sensitive, dermatologically acceptable, moisture vapor-permeable, and resistant to dissolution when exposed to water.

The method for making adhesives containing the pharmaceutical compositions of the present invention includes the following steps. First, the pharmaceutical composition is briefly mixed with the adhesive composition. Second, the resulting mixture is formed into a coat (i.e., film) using standard coating techniques. Finally, the mixture is dried to form a photostable, antimicrobially-active adhesive film which contains one or more medicinal agents.

The preferred amount of pharmaceutical composition in the adhesive material is between 5% and 40% by weight, depending on the end use, the concentration of medicinal agent needed, and the adhesive material used.

NON-ADHERENT MATERIALS

The method of treating a medical device composed of a non-adherent material with a pharmaceutical composition of the present invention depends on the nature of the non-adherent material. For non-adherent materials which are hydrophilic and absorbent in nature (e.g., alginate polymers in alginate dressings, cellulose polymers found in cellulosic dressings, and cotton gauze pads), the pharmaceutical composition can be applied directly to the non-adherent materials through spraying, dipping or other standard methods known to the art. The pharmaceutical composition is easily absorbed by the hydrophilic non-adherent material so as to provide a medical device which contains one or more medicinal agents and a stabilized ionized silver-based composition. The treated medical devices are photostable and antimicrobially active.

Medical devices composed of non-adherent materials which are hydrophobic or lipophilic in nature (e.g., catheter polymers such as silicone, PVC, and polyurethane) can also be treated with the pharmaceutical compositions of the present invention. This procedure involves applying the pharmaceutical composition to all surfaces of the medical device and allowing the pharmaceutical composition to absorb into or dry onto the material. Though not limited to any particular method, it is preferred that a pharmaceutical composition, in the form of a cream or solid at room temperature, be heated to achieve the liquid state, applied to the material, and allowed to cool. The application procedure may be accomplished by painting, spraying or dipping the medical device into the melted pharmaceutical composition; in some cases, the application procedure may involve infusing the pharmaceutical composition into a medical device.

Another method of treating medical devices composed of non-adherent materials which are hydrophobic or lipophilic in nature involves dipping or bathing the medical device in a bath which contains the pharmaceutical composition. The length of time the device is kept in the bath is dependent on many factors, including the type of material being treated, the dimensions of the material being treated, and the temperature of the solution. The duration can range from a few seconds to 24 hours. After the treated medical device has been given time to absorb the pharmaceutical composition into the non-adherent material, the excess pharmaceutical composition is eliminated from the device's surface. This can be accomplished by washing the treated device in a water bath for a few seconds and wiping the excess pharmaceutical composition off the device's surface with an absorptive material (e.g., paper towels) or by blowing the excess off the device's surface with a stream of air.

After the medical device has been treated, it will contain one or more medicinal agents and be infection-resistant against a broad spectrum of microbes. Since the device is light stable, no special packaging requirements are necessary.

FOAM ABSORBENT POLYMER MATRICES

Medical devices utilizing a foam absorbent polymer matrix ("foam objects") are extensively used in wound care because of the matrices ability to provide a moist wound microenvironment that is believed to promote the healing process at the wound site. However, foam absorbent polymer matrices (e.g., foam dressings) provide an excellent environment for the proliferation and overgrowth of microbes. These microbes, which proliferate on and in the foam matrix, can be shed from the foam object into the wound, leading to an infection. As a result, there is slower wound healing, added expense from treating the infection, etc.

The pharmaceutical compositions of the present invention can be used to treat foam objects so that they contain one or more medicinal agents and are antimicrobially active. Incorporating an antimicrobial agent within a foam object would help in preventing microbes from proliferating within the foam absorbent polymer matrix, which should, in turn, help minimize wound infections originating from the foam object.

The most widely used foam objects in wound care generally contain polyurethane foam matrices. The polyurethane foam matrices are typically produced by reacting a polyurethane prepolymer with a compound that is reactive to the polyurethane prepolymer. The polyurethane foam matrices may be created by standard means, such as injecting a gas into the mixture during the polymerization step. Alternatively, the polyurethane foam matrices may be created by using water as the reactive compound to cause the polymerization of the polyurethane prepolymer; water reacts with the isocyanate group in the polyurethane prepolymer, resulting in the formation of carbon dioxide, thus creating the polyurethane foam matrix.

The present invention contemplates a method of making a foam object using the pharmaceutical compositions of the present invention by infiltrating the pharmaceutical compositions directly into the foam matrix. The present invention contemplates the use of several different infiltration methods, including: i) applying pharmaceutical compositions to the surface of the foam matrix by spraying, painting, coating, etc., ii) submerging the foam matrix into a volume of pharmaceutical compositions, and iii) wicking the pharmaceutical compositions into the foam matrix. Of course, other standard means of applying solutions to foam matrices may be used to infiltrate the pharmaceutical compositions of the present invention.

While the infiltration method described in the preceding paragraph can produce foam objects that contain one or more medicinal agents and antimicrobial, stabilized ionized silver-based compositions, it is not the optimal method because it requires a "secondary" step during the production process of the foam object; briefly, an additional manufacturing step must be performed after the foam matrix has been produced to incorporate the pharmaceutical compositions therein. This "secondary" step results in the need for additional equipment, e.g., sprayers, coaters, etc., to apply the pharmaceutical compositions, thereby increasing costs.

An alternative method for imparting medicinal properties and antimicrobial protection to polyurethane foam objects involves introducing the pharmaceutical compositions of the present invention into the polymerization reaction which forms the foam matrix. This method comprises the following steps: (a) providing pharmaceutical compositions produced in accordance with the present invention; (b) directly incorporating the pharmaceutical compositions during the production of the foam matrix; and (c) drying the foam matrix. This method eliminates the "secondary" manufacturing step described above, thereby saving time and money and avoiding the need for additional equipment.

HYDROCOLLOID ABSORBENT POLYMER MATRICES

The pharmaceutical compositions of the present invention may also be used in the preparation of medical devices which have a hydrocolloid absorbent polymer matrix (e.g., hydrocolloid dressings) so that the medical device contains one or more medicinal agents and is antimicrobially active. Medical devices utilizing a hydrocolloid absorbent polymer matrix ("hydrocolloid objects") are also extensively used in wound care because of their ability to provide a moist wound microenvironment which, as described above, is believed to promote the healing process.

In addition to providing a moist wound microenvironment, hydrocolloid objects have the ability to absorb several times their weight in wound exudate. This is a major benefit when hydrocolloid objects are used in heavily exudating wounds. However, after having absorbed wound exudate, the hydrocolloid absorbent polymer matrix provides an excellent microenvironment for the proliferation and overgrowth of microbes. These microbes can shed from the hydrocolloid object into the wound, which can lead to infection. In turn, these infections can result in, among other things, slow wound healing and added expense associated with treating the infection. Furthermore, these microbes can result in the hydrocolloid object becoming malodorous, necessitating frequent changing.

Incorporating an antimicrobial agent with the hydrocolloid object helps prevent microbes from proliferating within the hydrocolloid absorbent polymer matrix, which in turn minimizes wound infections that originate on the hydrocolloid object. Furthermore, preventing microbial growth and proliferation prevents the hydrocolloid object from becoming malodorous.

Methods for producing absorbent hydrocolloid polymer matrices for use in medical devices are well known in the art. For example, in U.S. Pat. No. 3,339,546, a hydrocolloid absorbent polymer matrix is described which is a mixture of a water-soluble or swellable hydrocolloid material and a water-soluble, viscous, rubber-like elastic binder. Examples of the hydrocolloid materials include carbowax, vinyl polymers such as polyvinyl alcohol, polyvinyl pyrrolidone and polyvinylacetate; cellulose derivatives such as ethyl cellulose, methyl cellulose, carboxymethyl cellulose; and natural gums such as guar, acacia, and pectins. Examples of the viscous binders include natural rubber, elastomeric silicone polymers, polyurethane elastomers, and rubbery polymers such as polyisobutylene, polyisoprene and polybutadiene.

In accordance with the present invention, one method for imparting medicinal properties and antimicrobial protection to hydrocolloid objects involves incorporating the pharmaceutical compositions of the present invention during the process of manufacturing the hydrocolloid absorbent polymer matrix. This method comprises the following steps: (a) providing pharmaceutical compositions produced in accordance with the present invention; (b) mixing the pharmaceutical compositions with the water-soluble or swellable hydrocolloid materials; (c) admixing the hydrocolloid material/pharmaceutical compositions with the water-soluble, viscous, rubber-like elastic binder; (d) coating, molding or extruding the pharmaceutical compositions/hydrocolloid absorbent polymer matrix; and (e) drying the hydrocolloid absorbent polymer matrix using standard methods known to the art.

It is preferred that the finished hydrocolloid object have a final composition wherein the hydrocolloid absorbent polymer matrix range s from 40% to 90% of the total weight of the hydrocolloid object and the pharmaceutical compositions comprise 10% to 60% of the total weight of the hydrocolloid object. It is also preferred that the resulting pharmaceutical compositions/hydrocolloid absorbent polymer matrix be coated, molded or extruded to provide a matrix layer 0.01 to 15 millimeters thick; of course these limits can be exceeded if a greater or lesser amount of pharmaceutical composition is required. The resulting pharmaceutical compositions/absorbent hydrocolloid polymer matrix can be coated directly on flexible backing materials (e.g., films, foams, and foils), depending on its end use. Likewise, the pharmaceutical compositions/hydrocolloid absorbent polymer matrix can be coated and dried on a release liner and later transferred to a thin film or other flexible backing material.

EXPERIMENTAL

In the disclosure which follows, the following abbreviations apply: L (liters); ml (milliliters); µl (microliters); kg (kilograms); g (grams); mg (milligrams); µg (micrograms); cm (centimeters); mm (millimeters); meq (milliequivalents); °C. (degrees Centigrade); MW and M.W. (molecular weight); Å (Ångstroms); cps (Centipoise); MHA (Mueller Hinton Agar); ZOI (zone of inhibition); PEG (polyethylene glycol); PVC (polyvinyl chloride); CFU (colony forming units); I.V. (intravenous); Aldrich (Aldrich Chemical Co., Milwaukee, Wis.); BASF (Ludwigschafen, Germany); Cook (Cook Composites and Polymers, Kansas City, Mo.); Ethicon (Ethicon, Inc., Summerville, N.J.); Hampshire (Hampshire Chemical Company; Lexington, Mass.); Johnson & Johnson Medical, Inc. (Arlington, Tex.); Smith-Kline Beecham (Philadelphia, Pa.).

The following examples serve to illustrate certain preferred embodiments and aspects of the present invention and are not to be construed as limiting the scope thereof. As will be apparent to those skilled in the art, substitutions, alterations, and modifications, as well as different uses of the pharmaceutical compositions, are possible in the practice of the present invention without departing from the spirit or scope thereof.

EXAMPLE 1

Stabilized Silver-Based Antimicrobial Composition

An antimicrobial ionized silver-based composition was prepared for use in the subsequent preparation of the pharmaceutical compositions of the present invention.

An ionized silver-based composition (nominally 0.4% silver nitrate and 2.5% sodium chloride) was produced by stirring 4.32 ml of a 5 meq/ml silver nitrate water solution and 50 ml of deionized water into 800 grams of polyethylene glycol (M.W. 600). While this mixture was being stirred at a high rate of speed, 100 ml of a 4 meq/ml sodium chloride water solution was added. After constant stirring overnight, a clear solution—an ionized silver-based composition—formed which had no precipitate and was light stable. Placing some of this composition onto a cotton gauze pad and exposing it to light caused no discoloration of the gauze pad. The ratio of chloride anions to silver cations in the resulting solution was 18.5 to 1.

In the examples that follow, the stable antimicrobial composition produced in this example is referred to as the "Stabilized Ionized Silver-Based Composition".

EXAMPLE 2

Unstable Silver Nitrate/PEG Composition

An unstable ionized silver-based composition was prepared for use as a control in evaluating the pharmaceutical compositions of the present invention.

An unstable ionized silver-based composition (nominally 0.4% silver nitrate) was produced by stirring 0.1 ml of a 5 meq/ml silver nitrate water solution into 21.25 grams of polyethylene glycol (M.W. 600). Placing some of this composition onto a cotton gauze pad and exposing it to light caused discoloration of the gauze pad. In the examples that follow, this composition is referred to as "Unstable Silver Nitrate/PEG Composition."

EXAMPLE 3

Pharmaceutical Compositions Comprising Mupirocin

This example describes the preparation and photostability of pharmaceutical compositions comprising the medicinal agent mupirocin and either the Stabilized Ionized Silver-Based Composition of Example 1 or the Unstable Silver Nitrate/PEG Composition of Example 2.

A 0.05% mupirocin-PEG composition was produced by melting 1 g of 2% mupirocin ointment (Bactroban®, Smith-Kline Beecham; each gram containing 20 mg mupirocin in a polyethylene glycol ointment base) in 3 g of polyoxyethylene glycol (M.W. 600). An antimicrobial photostable pharmaceutical composition ("Test Composition I") was produced by melting and mixing together 0.25 g of the 0.05% mupirocin-PEG composition with 0.25 g of the Stabilized Ionized Silver-Based Composition of Example 1. Test Composition 1, when in its melted state, was a clear colorless solution. No discoloration was observed when exposed to light. After 72 hours of continuous exposure to ambient room light, no change in appearance developed. Test Composition 1 was deemed to be photostable and has use as a broad spectrum antimicrobial.

A control pharmaceutical composition ("Control Composition I") was produced by melting and mixing together 0.25 g of the 0.05% mupirocin-PEG composition described above with 0.25 g of the Unstable Silver Nitrate/PEG Composition of Example 2. This Control Composition I, when in its melted state, was a clear solution. However, within minutes of mixing the two components, the solution began to discolor upon exposure to light, changing from a clear, colorless solution to a light brown solution. This discoloration continued to deepen with continued exposure to light. Control Composition I was deemed not to demonstrate photostability.

EXAMPLE 4

Pharmaceutical Compositions Comprising Mafenide

This example describes the preparation and photostability of pharmaceutical compositions comprising the medicinal agent mafenide and either the Stabilized Ionized Silver-Based Composition of Example 1 or the Unstable Silver Nitrate/PEG Composition of Example 2.

A 1.0% mafenide-PEG composition was produced by dissolving 0.025 g of mafenide (p-(aminomethyl) benzenesulfonamide) in 2.475 g of polyoxyethylene glycol (M.W. 600). An antimicrobial photostable pharmaceutical composition ("Test Composition II") was produced by mixing together 2.5 g of the 1.0% mafenide-PEG composition with 2.5 g of the Stabilized Ionized Silver-Based Composition of Example 1. The resulting Test Composition II had a final concentration of 0.5% mafenide and 0.2% stabilized silver nitrate. When in its melted state, Test Composition II was a clear solution which was yellow in color. No change in color developed when Composition II was exposed to light. After 72 hours of continuous exposure to ambient room light, no change in appearance was observed. Test Composition II was deemed to be photostable and has use as a broad spectrum topical antimicrobial.

A control pharmaceutical composition ("Control Composition II") was produced by mixing together 2.5 g of the 1.0% mafenide-PEG composition described above with 2.5 g of the Unstable Silver Nitrate/PEG Composition of Example 2. Immediately after mixing the two components, this Control Composition II was a clear solution which had a yellow color. However, within minutes of mixing the two components, the composition began to darken when exposed to light, changing from a yellow-colored solution to a brown solution. Additionally, a dark precipitate began to form. The solution and precipitate continued to darken with continued exposure to light. Control Composition II was deemed to be photo-unstable.

EXAMPLE 5

Pharmaceutical Compositions Comprising Metronidazole

This example describes the preparation and photostability of pharmaceutical compositions comprising the medicinal agent metronidazole and either the Stabilized Ionized Silver-Based Composition of Example 1 or the Unstable Silver Nitrate/PEG Composition of Example 2.

A 1.0% metronidazole-PEG composition was produced by dissolving 0.025 g of metronidazole in 2.475 g of polyoxyethylene glycol (M.W. 600). An antimicrobial photostable pharmaceutical composition ("Test Composition III") was produced by mixing together 2.5 g of the 1.0% metronidazole-PEG composition with 2.5 g of the Stabilized Ionized Silver-Based Composition of Example 1. The resulting Test Composition III had a final concentration of 0.5% metronidazole and 0.2% stabilized silver nitrate. Test Composition III, when in its melted state, was a clear colorless solution. No change in color developed when the composition was exposed to light. After 72 hours of continuous exposure to ambient room light, no change in appearance was observed. Test Composition III was deemed to be photostable, has use as a broad spectrum topical antimicrobial, and is especially useful in the treatment of malodorous wounds.

A control pharmaceutical composition ("Control Composition III") was produced by mixing together 2.5 g of the 1.0% metronidazole-PEG composition described above with 2.5 g of the Unstable Silver Nitrate/PEG Composition of Example 2. Immediately after mixing the two components, this Control Composition III was a clear colorless solution. However, when exposed to light over a 3-hour period, Control Composition III began to change into a translucent solution, which had a dark gray color. This Control Composition III continued to darken with continued exposure to light and was deemed to be photo-unstable.

EXAMPLE 6

Pharmaceutical Compositions Comprising Chlorhexidine Gluconate

This example describes the preparation and photostability of pharmaceutical compositions comprising the medicinal agent chlorhexidine gluconate and either the Stabilized Ionized Silver-Based Composition of Example 1 or the Unstable Silver Nitrate/PEG Composition of Example 2.

An antimicrobial photostable pharmaceutical composition ("Test Composition IV") was produced by mixing together 0.1 g of a 20.0% chlorhexidine gluconate solution with 5.0 g of the Stabilized Ionized Silver-Based Composition of Example 1. The resulting Test Composition IV had a final concentration of 0.02% chlorhexidine gluconate and 0.4% stabilized silver nitrate. This pharmaceutical composition, when in its melted state, was a clear, colorless solution. No discoloration developed when the composition was exposed to light. After 72 hours of continuous exposure to ambient room light, no change in appearance was observed. Test Composition IV was deemed to be photostable and has use as a broad spectrum topical antimicrobial.

A control pharmaceutical composition ("Control Composition IV") was produced by mixing together 0.01 g of a 20% chlorhexidine gluconate solution with 5.0 g of the Unstable Silver Nitrate/PEG Composition of Example 2. Upon mixing the two components, a white precipitate formed. When exposed to light over a 3-hour period, Control Composition IV, as well as the precipitate in the composition, changed to a dark brown color. Control Composition IV kept darkening with continued exposure to light and was deemed to be photo-unstable.

EXAMPLE 7

Pharmaceutical Compositions Comprising Nitrofurazone

This example describes the preparation and photostability of pharmaceutical compositions comprising the medicinal agent nitrofurazone and either the Stabilized Ionized Silver-Based Composition of Example 1 or the Unstable Silver Nitrate/PEG Composition of Example 2.

A 1.0% nitrofurazone-PEG composition was produced by dissolving 0.025 g of nitrofurazone in 2.475 g of polyoxyethylene glycol (M.W. 600). An antimicrobial photostable pharmaceutical composition ("Test Composition V") was produced by mixing together 2.5 g of the 1.0% nitrofurazone-PEG composition with 2.5 g of the Stabilized Ionized Silver-Based Composition of Example 1. The resulting Test Composition V had a final concentration of 0.5% nitrofurazone and 0.2% stabilized silver nitrate. Test Composition V, when in its melted state, was a clear solution which had a yellow color. No change in color developed when the composition was exposed to light. After 72 hours of continuous exposure to ambient room light, no change in appearance was observed. Test Composition V was deemed to be photostable and has use as a broad spectrum topical antimicrobial.

A control pharmaceutical composition ("Control Composition V") was produced by mixing together 2.5 g of the 1.0% nitrofurazone-PEG composition described above with 2.5 g of the Unstable Silver Nitrate/PEG Composition of Example 2. Immediately after mixing the two components, this Control Composition V was a clear solution with a yellow color. However, when exposed to light over a 24-hour period, the solution darkened to an orange-brown color. Control Composition V kept darkening with continued exposure to light. This composition was deemed to be photo-unstable.

EXAMPLE 8

Pharmaceutical Compositions Comprising Salicylic Acid

This example describes the preparation and photostability of pharmaceutical compositions comprising the medicinal agent salicylic acid and either the Stabilized Ionized Silver-Based Composition of Example 1 or the Unstable Silver Nitrate/PEG Composition of Example 2.

A 10% salicylic acid-PEG composition was produced by dissolving 0.5 g of salicylic acid in 4.5 g of polyoxyethylene glycol (M.W. 600). An antimicrobial photostable pharmaceutical composition ("Test Composition VI") was produced by mixing together 2.5 g of the 10.0% salicylic acid-PEG composition with 2.5 g of the Stabilized Ionized Silver-Based Composition of Example 1. The resulting Test Composition VI had a final concentration of 5% salicylic acid and 0.2% stabilized silver nitrate. Test Composition VI, when in its melted state, was a clear, colorless solution. No change in color developed when the composition was exposed to light. After 72 hours of continuous exposure to ambient room light, no change in appearance was observed. Test Composition VI was deemed to be photostable. This pharmaceutical composition has use as a topical keratolytic composition possessing antimicrobial properties to prevent infection at the treatment site.

A control pharmaceutical composition ("Control Composition VI") was produced by mixing together 2.5 g of the 10.0% salicylic acid-PEG composition described above with 2.5 g of the Unstable Silver Nitrate/PEG Composition of Example 2. Immediately after mixing the two components, Control Composition VI was a clear solution with a yellow color. Over a 3-hour period, when exposed to light, the solution changed to a pink color. Control Composition VI continued to discolor with continued exposure to light. This composition was deemed to be photo-unstable.

EXAMPLE 9

Pharmaceutical Compositions Comprising PABA

This example describes the preparation and photostability of pharmaceutical compositions comprising the medicinal agent PABA and either the Stabilized Ionized Silver-Based Composition of Example 1 or the Unstable Silver Nitrate/PEG Composition of Example 2.

A 5% PABA (para-aminobenzoic acid)-PEG composition was produced by dissolving 0.25 g of PABA in 4.75 g of polyoxyethylene glycol (M.W. 600). An antimicrobial photostable pharmaceutical composition ("Test Composition VII") was produced by mixing together 2.5 g of the 5.0% PABA-PEG composition with 2.5 g of the Stabilized Ionized Silver-Based Composition of Example 1. Test Composition VII had a final concentration of 2.5% PABA and 0.2% stabilized silver nitrate. Test Composition VII, when in its melted state, was a clear solution with a pale yellow color. No change in color developed when the composition was exposed to light. After 72 hours of continuous exposure to ambient room light, no change in appearance was observed; thus, Test Composition VII was deemed to be photostable. This pharmaceutical composition has use as a topical sunscreen composition possessing antimicrobial properties to prevent a secondary infection when applied topically to blistered wounds from previously sunburned skin.

A control pharmaceutical composition ("Control Composition VII") was produced by mixing together 2.5 g of the 5.0% PABA-PEG composition described above with 2.5 g of the Unstable Silver Nitrate/PEG Composition of Example 2. Immediately after mixing the two components, this Control Composition VII was a clear solution with a deep, dark orange color. Over a 24-hour period, when exposed to light, the composition turned translucent with a deep purple/black color. Control Composition VII kept discoloring with continued exposure to light and was deemed to be photo-unstable.

EXAMPLE 10

Pharmaceutical Compositions Comprising Hydrocortisone

This example describes the preparation and photostability of pharmaceutical compositions comprising the medicinal agent hydrocortisone and either the Stabilized Ionized Silver-Based Composition of Example 1 or the Unstable Silver Nitrate/PEG Composition of Example 2.

A 0.4% hydrocortisone-PEG composition was produced by mixing 0.02 g of hydrocortisone in 4.98 g of polyoxyethylene glycol (M.W. 600). An antimicrobial photostable pharmaceutical composition ("Test Composition VIII") was produced by mixing together 2.5 g of the 0.4% hydrocortisone PEG composition with 2.5 g of the Stabilized Ionized Silver-Based Composition of Example 1. The resulting Test Composition VIII had a final concentration of 0.2% hydrocortisone and 0.2% stabilized silver nitrate. Test Composition VIII, when in its melted state, was a clear, colorless solution. No change in color developed when the composition was exposed to light. After 72 hours of continuous exposure to ambient room light, no change in appearance was observed, and Test Composition VIII was deemed to be photostable. Test Composition VIII has use as an anti-inflammatory and an anti-itch treatment possessing antimicrobial properties to prevent a secondary infection when applied topically to blistered wounds caused by dermatitis, insect bite, poison ivy, etc.

A control pharmaceutical composition ("Control Composition VIII") was produced by mixing together 2.5 g of the 0.4% hydrocortisone-PEG composition described above with 2.5 g of the Unstable Silver Nitrate/PEG Composition of Example 2. Immediately after mixing the two components, this Control Composition VIII was a clear solution. Over a 24-hour period, when exposed to light, the solution turned orange-brown in color. Control Composition VIII continued to discolor with continued exposure to light. This composition was considered to be photo-unstable.

EXAMPLE 11

Pharmaceutical Compositions Comprising Lidocaine

This example describes the preparation and photostability of pharmaceutical compositions comprising the medicinal agent lidocaine and either the Stabilized Ionized Silver-Based Composition of Example 1 or the Unstable Silver Nitrate/PEG Composition of Example 2.

A 0.4% lidocaine-PEG composition was produced by mixing 0.02 g of lidocaine in 4.98 g of polyoxyethylene glycol (M.W. 600). An antimicrobial photostable pharmaceutical composition ("Test Composition IX") was produced by mixing together 2.5 g of the 0.4% lidocaine-PEG composition with 2.5 g of the Stabilized Ionized Silver-Based Composition of Example 1. The resulting Test Composition IX had a final concentration of 0.2% lidocaine and 0.2% stabilized silver nitrate. Test Composition IX, when in its melted state, was a clear, colorless solution. After 72 hours of continuous exposure to ambient room light, no change in appearance was observed. Test Composition IX was deemed to be photostable and has use as a topical anesthetic possessing antimicrobial properties to prevent a secondary infection when applied to exposed tissues or wounds.

A control pharmaceutical composition ("Control Composition IX") was produced by mixing together 2.5 g of the 0.4% lidocaine-PEG composition described above with 2.5 g of the Unstable Silver Nitrate/PEG Composition of Example 2. Immediately after mixing the two components, this Control Composition IX, while remaining clear, turned dark red-orange in color. Over a 24-hour period, when exposed to light, the solution continued to deepen in color making the solution appear translucent. Control Composition IX continued to deepen in discoloration with continued exposure to light and was considered to be photo-unstable.

EXAMPLE 12

Pharmaceutical Compositions Comprising Pramoxine Hydrochloride

This example describes the preparation and photostability of pharmaceutical compositions comprising the medicinal agent pramoxine hydrochloride and either the Stabilized Ionized Silver-Based Composition of Example 1 or the Unstable Silver Nitrate/PEG Composition of Example 2.

A 0.4% pramoxine hydrochloride-PEG composition was produced by mixing 0.02 g of pramoxine hydrochloride in 4.98 g of polyoxyethylene glycol (M.W. 600). An antimicrobial photostable pharmaceutical composition ("Test Composition X") was produced by mixing together 2.5 g of the 0.4% pramoxine hydrochloride-PEG composition with 2.5 g of the Stabilized Ionized Silver-Based Composition of Example 1. The resulting Test Composition X had a final concentration of 0.2% pramoxine hydrochloride and 0.2% stabilized silver nitrate. Test Composition X, when in its melted state, was a clear, colorless solution. After 72 hours of continuous exposure to ambient room light, no change in appearance was observed. Test Composition X was deemed to be photostable. This pharmaceutical composition has use as a topical anesthetic possessing antimicrobial properties to prevent a secondary infection when applied to exposed tissues or wounds.

A control pharmaceutical composition ("Control Composition X") was produced by mixing together 2.5 g of the 0.4% pramoxine hydrochloride-PEG composition described above with 2.5 g of the Unstable Silver Nitrate/PEG Composition of Example 2. Immediately upon mixing the two components in Control Composition X, a milky-white precipitate developed. Over a 24-hour period, when exposed to light, the composition and the precipitate changed to a chocolate brown color. Control Composition X continued to deepen in discoloration with continued exposure to light and was deemed to be photo-unstable.

EXAMPLE 13

Pharmaceutical Compositions Comprising Chlorhexidine In Combination With Different Silver Salts The experiments of this example were performed to further demonstrate the importance of using a stabilized ionized silver-based composition in making photostable pharmaceutical compositions of the present invention. This example describes the preparation and photostability of pharmaceutical compositions comprising the medicinal agent chlorhexidine and different silver salts. Specifically, this example describes pharmaceutical compositions comprising chlorhexidine and either the Stabilized Ionized Silver-Based Composition of Example 1, the Unstable Silver Nitrate/PEG Composition of Example 2, a silver acetate/PEG composition, or a silver sulfadiazine/PEG composition.

An antimicrobial pharmaceutical composition ("Test Composition XI") was produced by mixing together 2.5 g of a 1.0% chlorhexidine-PEG composition with 2.5 g of the Stabilized Ionized Silver-Based Composition of Example 1. The resulting Test Composition XI had a final concentration of 0.5% chlorhexidine and 0.2% stabilized silver nitrate. Test Composition XI, when in its melted state, was a clear, colorless solution. After 72 hours of continuous exposure to ambient room light, no change in appearance was observed. Test Composition XI was deemed to be photostable. This pharmaceutical composition has use as a topical antimicrobial with a broad spectrum of antimicrobial activity.

A control pharmaceutical composition ("Control Composition XIa") was produced by mixing together 2.5 g of a chlorhexidine-PEG composition with 2.5 g of the Unstable Silver Nitrate/PEG Composition of Example 2. Immediately upon mixing the two components, this Control Composition XIa changed to a yellow color. Within 10 minutes, when exposed to light, the composition turned to a dark rust color. Over a 24-hour period, this composition continued to darken, and a black precipitate formed. Control Composition XIa, which uses silver nitrate in PEG, was deemed to be photo-unstable.

A second control pharmaceutical composition ("Control Composition XIb") was made that utilized silver acetate as the silver salt. A 0.4% silver acetate-PEG composition was produced by dissolving 0.02 g of silver acetate in 4.98 g of PEG. Control Composition XIb was then produced by mixing together 2.5 g of a chlorhexidine-PEG composition with 2.5 g of the 0.4% silver acetate PEG composition. Immediately upon mixing the two components, Control Composition XIb became cloudy, with a light orange-brown color. Over a 24-hour period, the composition darkened to a deep red-brown color and a dark precipitate settled. Control Composition XIb, which uses silver acetate in PEG, was considered to be photo-unstable.

A third control pharmaceutical composition ("Control Composition XIc") was made that utilized silver sulfadiazine as the silver salt. A 0.4% silver sulfadiazine-PEG composition was produced by combining 0.02 g of silver sulfadiazine in 4.98 g of PEG and mixing thoroughly until the silver sulfadiazine was dispersed in the PEG. Control Composition XIc was produced by mixing together 2.5 g of a chlorhexidine-PEG composition with 2.5 g of the 0.4% silver sulfadiazine-PEG composition. Immediately upon mixing the two components, Control Composition XIc had a cloudy, white appearance similar to the 0.4% silver sulfadiazine-PEG composition. Over a 48-hour period, the color of the composition change to a light brown. Control Composition XIc, which uses silver sulfadiazine in PEG, was deemed to be photo-unstable.

EXAMPLE 14

Photostability Of The Pharmaceutical Compositions

Examples 3–12 described the preparation and photostability of several pharmaceutical compositions contemplated by the present invention. This example describes in further detail the methodology for obtaining photostability data and summarizes that data.

As alluded to in the previous examples, the photostability of Test Compositions was evaluated over a 72-hour period and compared to Control Compositions containing the same medicinal agent but a different (i.e., unstable) ionized-silver base composition. The photostability study was performed by exposing the pharmaceutical compositions, which were stored in clear glass containers, to continuous ambient room fluorescent light. Periodically during the test period, the pharmaceutical compositions were examined for any changes in the appearance of color; in addition, the formation of a precipitate was noted.

The results of this photostability study are summarized in Table 3 below. Referring to Table 3, "——" means that no discoloration has occurred, while "+" means that discoloration has occurred. As described in Examples 3–12, the Control Compositions continued to discolor upon increased duration of exposure to light; thus, "++" means that there is more discoloration than "+", while "+++" means even more discoloration than "++".

TABLE 3

| Medicinal Agent | Composition Number | Test Composition <3 hrs. | Test Composition <24 hrs. | Test Composition <72 hrs. | Control Composition <3 hrs. | Control Composition <24 hrs. | Control Composition <72 hrs. |
|---|---|---|---|---|---|---|---|
| Mupirocin | I | ---- | ---- | ---- | + | ++ | +++ |
| Mafenide | II | ---- | ---- | ---- | + | ++ | +++ |
| Metronidazole | III | ---- | ---- | ---- | + | ++ | +++ |
| Chlorhexidine Gl. | IV | ---- | ---- | ---- | + | ++ | +++ |
| Nitrofurazone | V | ---- | ---- | ---- | + | ++ | +++ |
| Salicyclic Acid | VI | ---- | ---- | ---- | + | ++ | +++ |
| PABA | VII | ---- | ---- | ---- | + | ++ | +++ |
| Hydrocortisone | VIII | ---- | ---- | ---- | + | ++ | +++ |
| Lidocaine | IX | ---- | ---- | ---- | + | ++ | +++ |
| Paroximine | X | ---- | ---- | ---- | + | ++ | +++ |

The results demonstrate that all of the Test Compositions (i.e., the pharmaceutical compositions which combine a medicinal agent and the Stabilized Ionized Silver-Based Composition of Example 1) are photostable. Furthermore, none of the Test Compositions developed a precipitate during the 72 hour period. The fact that all of the Test Compositions showed absolutely no change in appearance suggests that the photostability should continue for very long periods.

In comparison, all of the Control Compositions showed photo-instability. That is to say, these compositions changed color from their initial appearance within the 72-hour test period. Furthermore, for practically all of the compositions being change in appearance began within the first 3 hours of the compositions being produced. Though the data is not presented in Table 3, it should be noted that Control Composition XIc, which used silver sulfadiazine in combination with chlorhexidine, discolored within 24 hours from the time it was produced; this is especially noteworthy because silver sulfadiazine is considered photostable when used alone. Though the practice of the present invention does not require an understanding of why these pharmaceutical compositions lacked photostability, it is believed that the lack of photostability was caused by the silver ion reacting with the medicinal agent, resulting in silver-medicinal agent salts which are light sensitive.

EXAMPLE 15

Antimicrobial Activity Of The Pharmaceutical Compositions

The previous examples were directed at the photostability of the pharmaceutical compositions of the present invention. This example examined the antimicrobial activity of the pharmaceutical compositions produced in those examples.

The pharmaceutical compositions of the previous examples were tested against *Staphylococcus aureus* and *Escherichia coli* using a standard zone of inhibition assay. This assay was performed by making a suspension of the test organism in 0.1% peptone water containing $10^{-6}$ to $10^{-8}$ CFU/ml. This suspension was used to make a lawn of a test organism on MHA plates using standard techniques. Wells (2 mm in diameter) were then made in the agar using standard techniques, and 0.1 µl of the pharmaceutical composition being tested was pipetted into each well. The culture plates were incubated at 37° C. for 24 hours.

Each pharmaceutical composition was then evaluated for antimicrobial activity by examining whether or not zones of inhibition were produced. If a zone of inhibition was produced, the pharmaceutical composition was considered to have antimicrobial activity. If no zone of inhibition was produced, then pharmaceutical composition was considered to have no antimicrobial activity. The results are summarized in Table 4. Referring to Table 4, "+++" means that a zone of inhibition was produced, while "-----" means that no zone of inhibition was produced.

TABLE 4

| Medicinal Agent | Composition Number | Test Composition Staph. aureous | Test Composition E. coli | Control Composition Staph. aureous | Control Composition E. coli |
|---|---|---|---|---|---|
| Mupirocin | I | +++ | +++ | +++ | +++ |
| Mafenide | II | +++ | +++ | +++ | ----- |
| Metronidazole | III | +++ | +++ | +++ | +++ |
| Chlorhexidine Gl. | IV | +++ | +++ | +++ | +++ |
| Nitrofurazone | V | +++ | +++ | +++ | +++ |
| Salicylic Acid | VI | +++ | +++ | +++ | +++ |
| PABA | VII | +++ | +++ | +++ | +++ |
| Hydrocortisone | VIII | +++ | +++ | +++ | +++ |
| Lidocaine | IX | +++ | +++ | +++ | +++ |
| Paroximine | X | +++ | +++ | +++ | +++ |

The results demonstrate that all pharmaceutical compositions which combined a medicinal agent and the Stabilized Ionized Silver-Based Composition of Example 1 were antimicrobially active. In comparison, one of the control pharmaceutical compositions (i.e., the composition containing mafenide) which combined a medicinal agent and the Unstable Silver Nitrate/PEG Composition of Example 2 did not demonstrate antimicrobial activity against *E. coli*. Though the practice of the present invention does not require an understanding of why this pharmaceutical composition lacked antimicrobial activity, it is believed that the lack of antimicrobial activity is a result of the silver ion reacting with the medicinal agent.

EXAMPLE 16

Staining of The Pharmaceutical Compositions

As previously indicated, one of the shortcomings of silver-containing topical preparations is that they cause staining of tissue. This example evaluated whether the silver in the pharmaceutical compositions of the present invention causes staining.

The staining study was performed using the Test Compositions and the Control Compositions produced in the Examples 3–12. Small samples of these pharmaceutical compositions were applied to a paper towel, and the paper towels were exposed to continuous ambient room fluorescent light for a period of 72 hours. Periodically during the test period, the paper towels were examined for any development of a dark color stain.

The results of this staining study are summarized in Table 5. Referring to Table 5, "—" means that no staining has occurred, while "+" means that staining has occurred. As discussed further below, the Control Compositions continued to stain (i.e., darken) upon increased duration of exposure; thus, "++" means that there is more staining than "+", while "+++" means even more staining than "++".

EXAMPLE 17

Stabilized Silver-Based Antimicrobial Cream Composition

An antimicrobial ionized silver-based cream composition was prepared for use in the subsequent preparation of pharmaceutical compositions of the present invention in a cream form.

An antimicrobial ionized silver-based cream composition was produced by melting 100 g of a polyethylene glycol cream mixture (63% PEG 600, 5% PEG 1000, 32% PEG 4000) and stirring in 0.47 ml of a 5 meq/ml silver nitrate water solution. While this mixture was being stirred at a high rate of speed, 3.8 ml of a 4 meq/ml sodium chloride water solution was added. This mixture was allowed to cool while being stirred to form a photostable antimicrobial ionized silver-based cream composition. The concentration of silver nitrate in this cream was nominally 0.4%, and the ratio of chloride anions to silver cations was 6.5 to 1.

In several of the examples that follow, the stable antimicrobial cream composition produced above is referred to as the "Stabilized Ionized Silver-Based Cream Composition" of Example 17.

TABLE 5

|                  |                     | Test Composition | | | Control Composition | | |
| --- | --- | --- | --- | --- | --- | --- | --- |
| Medicinal Agent  | Composition Number  | <3 hrs. | <24 hrs. | <72 hrs. | <3 hrs. | <24 hrs. | <72 hrs. |
| Mupirocin        | I   | ---- | ---- | ---- | ---- | +  | ++  |
| Mafenide         | II  | ---- | ---- | ---- | ---- | +  | +   |
| Metronidazole    | III | ---- | ---- | ---- | +    | +  | +++ |
| Chlorhexidine Gl.| IV  | ---- | ---- | ---- | +    | ++ | +++ |
| Nitrofurazone    | V   | ---- | ---- | ---- | +    | ++ | +++ |
| Salicyclic Acid  | VI  | ---- | ---- | ---- | ---- | +  | ++  |
| PABA             | VII | ---- | ---- | ---- | +    | +  | ++  |
| Hydrocortisone   | VIII| ---- | ---- | ---- | ---- | ++ | +++ |
| Lidocaine        | IX  | ---- | ---- | ---- | +    | ++ | +++ |
| Paroximine       | X   | ---- | ---- | ---- | ++   | +++| +++ |

All of the paper towels to which the Test Compositions were applied showed no change in appearance. These results demonstrate that all of the Test Compositions (i.e., the pharmaceutical compositions which combine a medicinal agent and the Stabilized Ionized Silver-Based Composition of Example 1) are nonstaining.

In contrast, all of the Control Compositions showed staining. The areas on the paper towel to which these compositions were applied darkened from their initial appearance within the 72-hour test period. Furthermore, for practically all of the Control Compositions, the change in appearance began within the first 24 hours of the compositions being produced. Though the data is not presented in Table 5, it should be noted that Control Composition XIc, which used silver sulfadiazine in combination with chlorhexidine, caused staining within 24 hours of the time it was applied to the paper towel; this is especially noteworthy because silver sulfadiazine is considered photostable and nonstaining when used alone. Though the practice of the present invention does not require an understanding of why these pharmaceutical compositions were staining, it is believed that the staining was caused by the silver ion reacting with the medicinal agent, resulting in the formation of silver-medicinal agent salts which are light sensitive and can cause staining.

EXAMPLE 18

Pharmaceutical Cream Composition Comprising Chlorhexidine Gluconate

This example describes the preparation of a pharmaceutical cream composition comprising the medicinal agent chlorhexidine gluconate and the Stabilized Ionized Silver-Based Cream Composition of Example 17.

A pharmaceutical composition in the form of a cream (Test Composition XII) was produced by heating, until melted, 10.0 g of the Stabilized Ionized Silver-Based Cream Composition of Example 17 and then stirring in 0.2 g of a 20.0% chlorhexidine gluconate solution. This mixture, while being stirred, was allowed to cool to form a photostable, non-staining cream. The resulting Test Composition XII had a final nominal concentration of 0.4% silver nitrate and 0.2% chlorhexidine gluconate. Test Composition XII has use as a broad spectrum topical antimicrobial with special utility in the prevention and treatment of infections in burn wounds.

EXAMPLE 19

Polyurethane Adhesive Film Containing A
Pharmaceutical Composition Comprising Pramoxine Hydrochloride This example first describes the preparation of a polyurethane adhesive material that can be used in conjunction with the pharmaceutical compositions of the present invention. Thereafter, this example describes the incorporation of the local anesthetic pramoxine hydrochloride into the polyurethane adhesive material.

A polyurethane adhesive was produced by first making an acetone oxime solution by dissolving 24.5 g of acetone oxime in 2.2 kg of deionized water. Next, the acetone oxime solution was mixed into 1.24 kg of a polyurethane prepolymer (Aquapol 035-0031, Cook). The mixture was stirred for 1 hour, during which time the polyurethane prepolymer reacted to form a polyurethane adhesive solution ("Polyurethane Adhesive Solution"). This Polyurethane Adhesive Solution had a viscosity of 6,475 cps. The Polyurethane Adhesive Solution was coated and dried, resulting in a tacky, adhesive film. This polyurethane adhesive film has use in conjunction with polymer film backings as a wound dressing.

A polyurethane adhesive film was then produced that contained the local anesthetic pramoxine hydrochloride ("Antimicrobial Pramoxine Hydrochloride Adhesive"). The Antimicrobial Pramoxine Hydrochloride Adhesive was produced by mixing 1 g of Test Composition X (Example 12) with 15.74 g of Polyurethane Adhesive Solution (described above). This Antimicrobial Pramoxine Hydrochloride Adhesive, when coated and dried, produces a tacky, adhesive film. The resulting adhesive film had a 0.03% silver nitrate concentration and a 0.03% pramoxine hydrochloride concentration.

The adhesive film is photostable and antimicrobially active, and can be laminated to dressing-backing materials to produce dressings which are antimicrobially active and that contain a topical anesthetic agent. Dressings with the Antimicrobial Pramoxine Hydrochloride Adhesive are especially useful in covering painful abrasive-type skin wounds and partial skin graft sites.

EXAMPLE 20

Polyurethane Adhesive Film Containing A Pharmaceutical Composition Comprising Chlorhexidine Gluconate To further illustrate the use of the pharmaceutical compositions of the present invention to produce adhesive films which contain both a medicinal agent and a stabilized ionized silver-based composition, this example describes the incorporation of the antimicrobial agent chlorhexidine gluconate into a polyurethane adhesive material.

An antimicrobial adhesive solution ("Antimicrobial CHG Adhesive") was made which contained the antimicrobial agent chlorhexidine gluconate and a stabilized ionized silver-based composition. The Antimicrobial CHG Adhesive was produced by mixing 1 g of Test Composition IV (Example 6) with 15.74 g of Polyurethane Adhesive Solution (Example 19). This Antimicrobial CHG Adhesive, when coated and dried, produced a tacky, adhesive film. The resulting adhesive film had a 0.06% silver nitrate concentration and a 0.03% chlorhexidine gluconate concentration.

The adhesive film is photostable and antimicrobially active. This adhesive film can be laminated to dressing-backing materials to produce dressings which are antimicrobially active. Dressings with the Antimicrobial CHG Adhesive are especially useful in covering I.V. sites to prevent infection.

EXAMPLE 21

Alginate Dressing Containing A Pharmaceutical Composition

This example illustrates the use of the pharmaceutical compositions of the present invention to treat a medical device which is made up of a non-adherent material.

An antimicrobial alginate dressing ("Antimicrobial Mafenide Alginate Dressing") was made which contained the antimicrobial agent mafenide acetate and a stabilized ionized silver-based composition. This dressing was produced by using an airbrush to spray 0.4 g of Test Composition II (Example 4) onto a 9.5 cm ×9.5 cm alginate dressing (Algosteril® Calcium Alginate Dressing; Johnson & Johnson) which weighed approximately 0.6 g. Test Composition II was absorbed by the alginate fibers of the dressing. The treated dressing had a nominal silver nitrate concentration of 0.08% and a nominal mafenide concentration of 0.2%. The Antimicrobial Mafenide Alginate Dressing was light-stable and antimicrobially active and is useful on malodorous wounds.

EXAMPLE 22

Suture Containing A Pharmaceutical Composition

This example further illustrates the use of the pharmaceutical compositions of the present invention to treat a medical device which is made up of a non-adherent material.

An antimicrobial suture ("Antimicrobial Hydrocortisone Suture") was made which contained hydrocortisone and a stabilized ionized silver-based composition. This suture was produced by dipping a silk suture (3-0, Ethicon Silk Black Braided, Ethicon) into a solution of Test Composition VIII (Example 10). The excess Test Composition VIII on the suture was wiped away using a paper towel. This treated suture did not change in appearance and was antimicrobially active. This Antimicrobial Hydrocortisone Suture is useful in suturing contaminated wounds and is especially useful in preventing tissue inflammation at the suture site.

EXAMPLE 23

Catheter Containing A Pharmaceutical Composition

This example still further illustrates the use of the pharmaceutical compositions of the present invention to treat a medical device which is made up of a non-adherent material.

An antimicrobial catheter ("Antimicrobial Catheter") was made which contained the antimicrobial chlorhexidine gluconate and a stabilized ionized silver-based composition. A polyurethane catheter (Straight Catheter, manufactured by Cook Catheter) was treated by first heating the Stabilized Ionized Silver-Based Cream Composition of Example 17 until it formed a liquid. The liquid composition was then applied onto the surface of the polyurethane catheter to provide, when cooled and solidified, a thin layer of the pharmaceutical composition. The Antimicrobial Catheter was photostable and antimicrobially active and is useful for placement in sites prone to catheter infections.

EXAMPLE 24

Foam Dressing Containing A Pharmaceutical Composition

This examples illustrates the use of the pharmaceutical compositions of the present invention to prepare a medical device which is made up of a foam polymer matrix.

A foam dressing ("Antimicrobial Foam Dressing") was made which contained chlorhexidine gluconate and a stabilized ionized silver-based composition. This Antimicrobial Foam Dressing was produced by first mixing 3.5 g of Test Composition IV (Example 6) with 5.5 g of a polyurethane prepolymer (Hypol 2002, Hampshire) and then immediately mixing in 5.5 g of water. The resulting mixture instantly began to react to form a foam. After 15 minutes, the foam was removed from its container and stored in the dark to allow it to dry. After drying, the resulting foam was sliced to produce foam dressings. These Antimicrobial Foam Dressings were light stable and antimicrobially active and can be used for a large variety of medical applications, including as an antimicrobial absorptive foam dressing.

EXAMPLE 25

Hydrocolloid Dressing Containing A Pharmaceutical Composition

This examples illustrates the use of the pharmaceutical compositions of the present invention to prepare a medical device which is made up of a hydrocolloid absorbent polymer matrix.

A hydrocolloid dressing ("Antimicrobial Mafenide Hydrocolloid Dressing") was made which contained mafenide and a stabilized ionized silver-based composition. The Antimicrobial Mafenide Hydrocolloid Dressing was produced by first mixing 2 g of Test Composition II (Example 4) with 4 g of sodium carboxymethyl cellulose. This treated carboxymethyl cellulose was then combined and mixed thoroughly with 4 g of a polyurethane prepolymer (Aquapol 035-0031, Cook Composites and Polymers). The resulting mixture was then pressed between a polyurethane film and a silicone-treated polyester liner to produce a 2.5 mm thick, treated hydrocolloid matrix. The treated hydrocolloid matrix was allowed to cure for 24 hours. The resulting Antimicrobial Mafenide Hydrocolloid Dressing was photostable and antimicrobially active and is useful on exudating, malodorous wounds.

From the above, it should be evident that the present invention provides for ionized silver-based antimicrobial compositions and processes for making such compositions that are suitable for use in the treatment and prevention of infections and for the treatment of medical devices to render them infection-resistant. It should be understood that the present invention is not limited to the specific compositions shown nor to the uses of the compositions described. In light of the foregoing disclosure, it will be apparent to those skilled in the art that substitutions, alterations, and modifications are possible in the practice of this invention without departing from the spirit or scope thereof.

I claim:

1. A pharmaceutical mixture, comprising:
   a) a non-silver-containing medicinal agent; and
   b) a silver ion-containing composition, said silver containing composition comprising an acyclic polyether polymer and a stabilizing anion, wherein said acyclic polyether polymer is selected from the group consisting of polyethylene glycol and polypropylene glycol, wherein said anion is selected from the group consisting of chloride, bromide, and iodide, and wherein the ratio of equivalents of said anion to equivalents of said silver ion is greater than 4 to 1 when said anion is chloride, is greater than 2.1 to 1 when said anion is bromide, and is greater than 1.1 to 1 when said anion is iodide, wherein said pharmaceutical mixture is photostable after 72 hours of continuous exposure to ambient room light.

2. The pharmaceutical mixture of claim 1, wherein said non-silver-containing medicinal agent is an antimicrobial agent.

3. The pharmaceutical mixture of claim 2, wherein said antimicrobial agent is selected from the group consisting of acyclovir, chloramphenicol, chlorhexidine, chlortetracycline, itraconazole, mafenide, metronidazole, mupirocin, nitrofurazone, oxytetracycline, penicillin, and tetracycline.

4. The pharmaceutical mixture of claim 2, wherein said pharmaceutical mixture has a broader spectrum of antimicrobial protection than said silver ion-containing composition.

5. The pharmaceutical mixture of claim 1, wherein said non-silver-containing medicinal agent is a steroid.

6. The pharmaceutical mixture of claim 5, wherein said steroid is selected from the group consisting of betamethasone benzoate, betamethasone valerate, desonide, fluocinolone acetonide, halcinonide, hydrocortisone, and metandienone.

7. The pharmaceutical mixture of claim 1, wherein said non-silver-containing medicinal agent is an anesthetic.

8. The pharmaceutical mixture of claim 7, wherein said anesthetic is selected from the group consisting of benzocaine, dibucaine, lidocaine, pramoxine hydrochloride and tetracaine.

9. A pharmaceutical mixture, comprising:
   a) a non-silver-containing antimicrobial agent;
   b) a composition comprising:
      i) a stabilizing acyclic polyether polymer wherein said acyclic polyether polymer is selected from the group consisting of polyethylene glycol and polypropylene glycol;
      ii) silver ion, wherein said silver ion is present in an amount ranging from $1 \times 10^{-6}$ to 1 meq of silver ion per gram of said acyclic polyether polymer;
      iii) a stabilizing anion wherein said anion is selected from the group consisting of chloride, bromide, and iodide, and wherein the ratio of equivalents of said anion to equivalents of said silver ion is greater than 4 to 1 when said anion is chloride, is greater than 2.1 to 1 when said anion is bromide, and is greater than 1.1 to 1 when said anion is iodide; and wherein said pharmaceutical mixture is photostable after 72 hours of continuous exposure to ambient room light.

10. The pharmaceutical mixture of claim 9, wherein said anion is chloride ion.

11. The pharmaceutical mixture of claim 10, wherein the ratio of equivalents of said chloride ion to equivalents of said silver ion is from 4-to-1 to 50-to-1.

12. The pharmaceutical mixture of claim 9, wherein said antimicrobial agent is selected from the group consisting of acyclovir, chloramphenicol, chlorhexidine, chlortetracycline, itraconazole, mafenide, metronidazole, mupirocin, nitrofurazone, oxytetracycline, penicillin, and tetracycline.

13. The pharmaceutical mixture of claim 9, wherein said pharmaceutical mixture has a broader spectrum of antimicrobial protection than said silver ion-containing composition.

14. A method of treating a device, comprising:
   a) providing:
      i) a medical device; and
      ii) a pharmaceutical mixture that is photostable after 72 hours of continuous exposure to ambient room light, comprising a non-silver-containing medicinal agent and a composition comprising a stabilizing acyclic polyether polymer wherein said acyclic polyether polymer is selected from the group consisting of polyethylene glycol and polypropylene glycol, a silver ion wherein said silver ion is present in an amount ranging from $1 \times 10^{-6}$ meq of silver ion per gram of said acyclic polyether polymer, and a stabilizing anion selected from the group consisting of chloride, bromide, and iodide; and b) applying said pharmaceutical mixture to said medical device, thereby treating said device.

15. The method of claim 14, wherein said device is selected from the group consisting of a medical implant, a wound care device, a drug delivery device, a body cavity device, and a personal protection device.

16. The method of claim 14, wherein the ratio of equivalents of said anion to equivalents of said silver ion is greater than 4 to 1 when said anion is chloride, greater than 2.1 to 1 when said anion is bromide, and greater than 1.1 to 1 when said anion is iodide.

17. The method of claim 14, wherein said non-silver-containing medicinal agent is an antimicrobial agent.

18. The method of claim 17, wherein said antimicrobial agent is selected from the group consisting of acyclovir, chloramphenicol, chlorhexidine, chlortetracycline, itraconazole, mafenide, metronidazole, mupirocin, nitrofurazone, oxytetracycline, penicillin, and tetracycline.

19. The method of claim 17, wherein said pharmaceutical mixture has a broader spectrum of antimicrobial protection than said silver ion-containing composition.

20. The method of claim 14, wherein said non-silver-containing medicinal agent is a steroid.

21. The method of claim 20, wherein said steroid is selected from the group consisting of betamethasone benzoate, betamethasone valerate, desonide, fluocinolone acetonide, halcinonide, hydrocortisone, and metandienone.

22. The method of claim 14, wherein said non-silver-containing medicinal agent is an anesthetic.

23. The method of claim 22, wherein said anesthetic is selected from the group consisting of benzocaine, dibucaine, lidocaine, pramoxine hydrochloride and tetracacine.

* * * * *